US010513708B2

(12) United States Patent
Dardick et al.

(10) Patent No.: US 10,513,708 B2
(45) Date of Patent: Dec. 24, 2019

(54) **DRO1 RELATED GENES INFLUENCE LATERAL ROOT ORIENTATION AND GROWTH IN *ARABIDOPSIS* AND *PRUNUS* SPECIES**

(71) Applicant: The United States of America, as Represented by the Secretary of Agriculture, Washington, DC (US)

(72) Inventors: Christopher D. Dardick, Shenandoah Junction, WV (US); Jessica M. Guseman, Charles Town, WV (US); Courtney A. Hollender, East Lansing, MI (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 6 days.

(21) Appl. No.: 15/703,434

(22) Filed: Sep. 13, 2017

(65) Prior Publication Data

US 2018/0094272 A1 Apr. 5, 2018

Related U.S. Application Data

(60) Provisional application No. 62/403,033, filed on Sep. 30, 2016.

(51) Int. Cl.
*C12N 15/82* (2006.01)
(52) U.S. Cl.
CPC ..... *C12N 15/8261* (2013.01); *C12N 15/8273* (2013.01)
(58) Field of Classification Search
None
See application file for complete search history.

(56) References Cited

U.S. PATENT DOCUMENTS

2017/0088846 A1 3/2017 Dardick et al.

OTHER PUBLICATIONS

Uga et al. Control of root system architecture by Deeper Rooting 1 increases rice yield under drought conditions. Nat Genet. Sep. 2013;45(9):1097-102. Epub Aug. 4, 2013 . (Year: 2013).*
Hollender et al. Molecular basis of angiosperm tree architecture. New Phytol. Apr. 2015;206(2):541-56. Epub Dec. 5, 2014 . (Year: 2015).*
Sabbadini et al. Peach (*Prunus persica* L.). Methods Mol Biol. 2015;1224:205-15. (Year: 2015).*
Petri et al. II Highly efficient transformation protocol for plum (*Prunus domestica* L.). Methods Mol Biol. 2012;847:191-9. (Year: 2012).*
Petri et al. Apricot (*Prunus armeniaca* L.). Methods Mol Biol. 2015;1224:111-9. (Year: 2015).*
Dong, Zhaobin et al., Pleiotropic effects of ZmLAZY1 on the auxin-mediated responses to gravity and light in maize shoot and inflorescences, Plant Signaling & Behavior, (2013) Landes Bioscience, 8:12, e27451-e27452-3.
Dong, Zhaobin et al., Maize LAZY1 Mediates Shoot Gravitropism and Inflorescence Development through Regulating Auxin , Transport, Auxin Signaling, and Light Response1[C][W], Plant Physiology, (2013),163:1306-1322.
Ge, Liangfa et al., Negative gravitropism in plant roots, Nature Plants (2016), 2:1-4.
Guseman, Jessica M. et al., DRO1 influences root system architecture in *Arabidopsis* and *Prunus* species, The Plant Journal (2017) 89:1093-1105.
Hollender, Courtney A. et al., Molecular basis of angiosperm tree architecture (Tanley Review), New Phytologist, (2015), 206: 541-556.
Howard III, Thomas P. et al., Identification of the Maize Gravitropism Gene lazy plant1by a Transposon-Tagging Genome Resequencing Strategy, PLOS One (2014), 9(1):1-12.
Ku, Lixia et al., Cloning and Characterization of a Putative TAC1Ortholog Associated with Leaf Angle in Maize (*Zea mays* L.), PLoS One, (2011), 6(6):1-7.
Li, Peijin et al., LAZY1 controls rice shoot gravitropism through regulating polar auxin transport, Cell Research, (2007) 17:402-410.
Rosquete, Michel Ruiz et al., An Auxin Transport Mechanism Restricts Positive Orthogravitropism in Lateral Roots, Current Biology, (2013), 23:817-822.
Uga, Yusaku et al., Control of root system architecture by Deeper Rooting 1 increases rice yield under drought conditions, Nature Genetics, (2013), 45(9):1097-1106.
Uga, Yusaku et al., Genetic improvement for root growth angle to enhance crop production, Breeding Science, (2015), 65:111-119.
Yoshihara, Takeshi et al., Identification of the Gravitropism-Related Rice Gene LAZY1 and Elucidation of LAZY1-Dependent and -Independent Gravity Signaling Pathways, Plant Cell Physiol. (2007), 48(5): 678-688.
Yoshihara, Takeshi et al., AtLAZY1 is a signal component required for gravitropism of the *Arabidopsis thaliana* inflorescene, The Plant Journal, (2013), 74:267-279.

(Continued)

*Primary Examiner* — Cynthia E Collins
(74) *Attorney, Agent, or Firm* — John D. Fado; Ariel L. Atkinson

(57) ABSTRACT

Root orientation, or angle, is an important component of root architecture and depth of the root system. We have determined that DRO1 and DRO1-related genes are present across diverse plant phyla and fall within the IGT gene family. DRO1, present in both *Arabidopsis* and peach, displayed root specific expression patterns. AtDRO1 is predominantly expressed in both the root vasculature and root tips in a distinct developmental pattern. Mutation of AtDRO1 led to more horizontal lateral root angles; overexpression of AtDRO1 under a constitutive promoter reduced lateral root angles and resulted in shoot phenotypes including upward leaf curling, shortened siliques, and narrow lateral branch angles. Over-expression of PpeDRO1 in plum (*Prunus domestica*) led to deeper rooting phenotypes. These data establish that DRO1-related genes serve a role in altering root architecture, providing a method for drought avoidance.

14 Claims, 20 Drawing Sheets
(16 of 20 Drawing Sheet(s) Filed in Color)
Specification includes a Sequence Listing.

(56) References Cited

OTHER PUBLICATIONS

Yu, Baisheng et al., TAC1, a major quantitative trait locus controlling tiller angle in rice, The Plant Journal, (2007) 52:891-898.
Guseman, Jessica et al., "Deeper rooting 1 controls root orientation and depth in *Arabidopsis* and *Prunus* species", In: 33rd Annual Mid-Atlantic Plant Molecular Biology Society, National Wildlife Visitor Center, US, (2016), p. 18.
NCBI Reference Sequence: XP_008228169.1, Predicted: uncharacterized protein LOC103327608 [*Prunus mume*], (2016).
International Searching Authority, PCT/US2017/053487 for The United States of America, as Represented by the Secretary of Agriculture, International Filing Date Sep. 26, 2017.
Dardick, Chris et al., "PpeTAC1 promotes the horizontal growth of branches in peach trees and is a member of a functionally conserved gene family found in diverse plants species", (2013) The Plant Journal 75:618-630.
Blancaflor, Elison B. (ed.), "Analysis of Gravitropic Setpoint Angle Control in *Arabidopsis*",(2015) Chap. 4, Plant Gravitropism: Methods and Protocols, Methods in Molecular Biology, vol. 1309:31-41.
Roychoudhry, Suruchi et al., "Auxin Controls Gravitropic Setpoint Angle in Higher Plant Lateral Branches", (2013) Current Biology 23(15):1497-1504.

\* cited by examiner

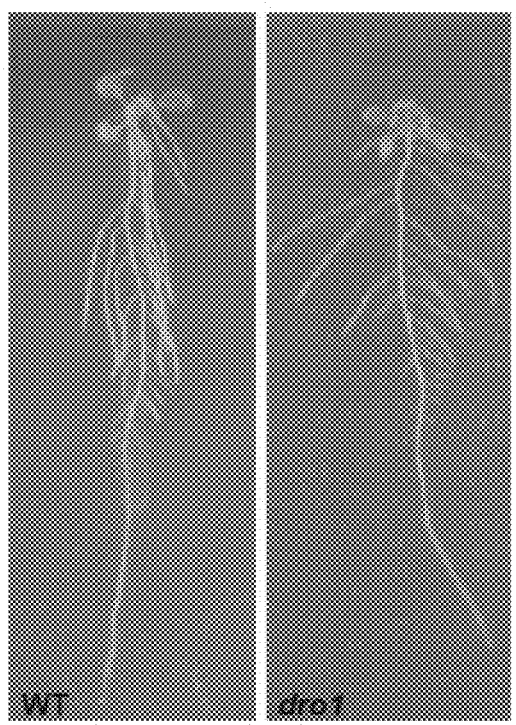
FIG. 2A
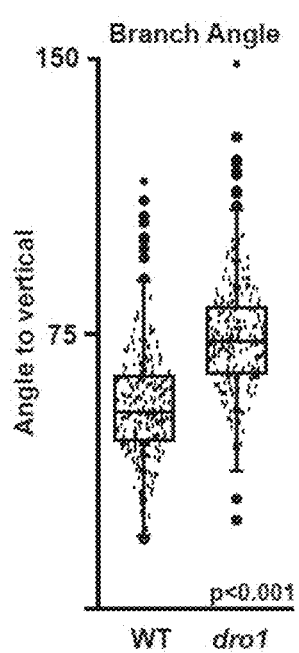 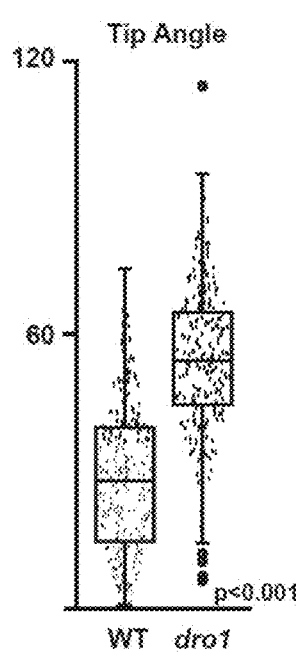 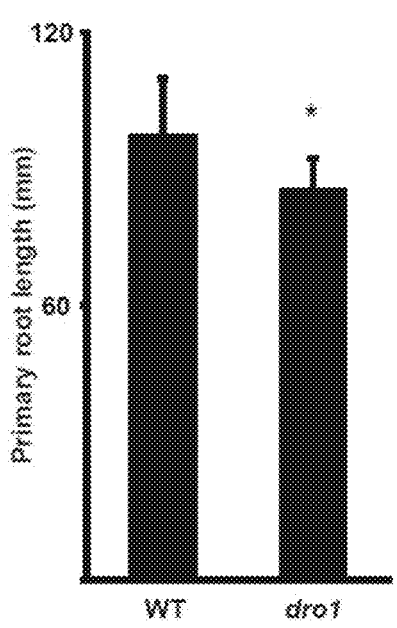
FIG. 2B  FIG. 2C

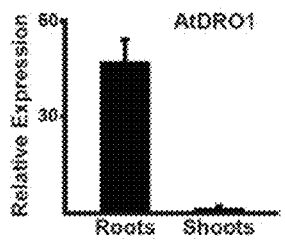
FIG. 4A
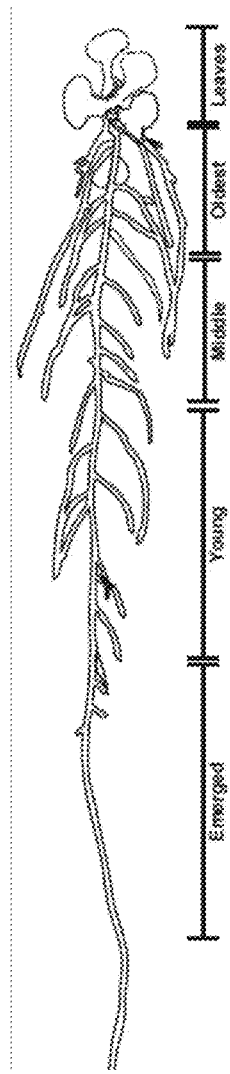
FIG. 4H
FIG. 4B
FIG. 4C
FIG. 4D
FIG. 4E
FIG. 4F
FIG. 4G
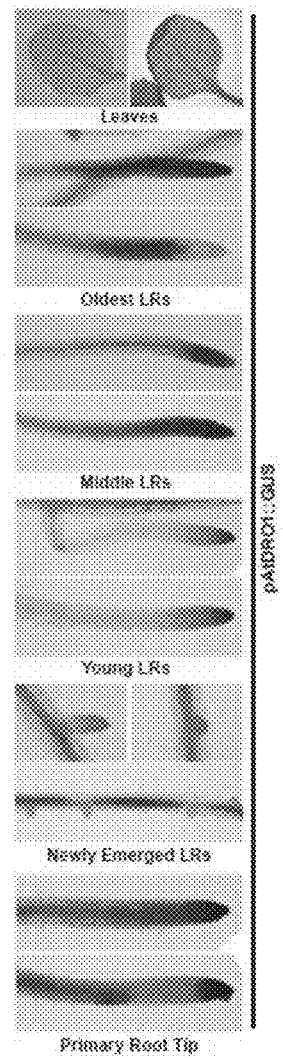

SEQUENCE LISTING

```
<160> NUMBER OF SEQ ID NOS: 18

<210> SEQ ID NO 1
<211> LENGTH: 807
<212> TYPE: DNA
<213> ORGANISM: Prunus persica

<400> SEQUENCE: 1
atgaagcttt ttggttggat gcaaaataag cttaatggaa agcaggggaa caagaaacca     60
aatacagttc ctattactac tcatcctgca aaacaagagc ctcgtgaaga attcagtgac    120
tggcctcatg gattactagc aattggaact tttggaaaca atgatttgaa agaaaatgca    180
gctgaaagcc aagatattca ggaagatcca acttcatcag aagaaatact agataaattc    240
actcctgaag aggttggcaa attacataaa gagttaacaa agctcttaac gcgaaaacca    300
aacatcgaaa aggaaatcgc agatcttcca ttggacagat ttctaaactg cccatcaagc    360
ttggaggttg atcggagaaa cagcaatgca ctttgctccg attcagcaga tgatcacaag    420
gatgaagaca ttgagaagac tattagtgtc atacttggta gatgcaaaga aatttgtgga    480
gataagaata agaaggcaat tgggaagaaa tctatttctt ttcttctcaa gaagatgttt    540
gtttgcagaa gtggatttgc accacaacca agtttgagag atacacttca agagtcaaga    600
atggagaagc ttttgagggt aatgcttaac aagaagatca tcaatccgca aggatcttct    660
cgagcagcat cgatgaagaa atacctggag gatagacaga ttccaacaaa gaaggaaagt    720
aacactgaag atgatacaaa agagaaaatt aataatggat gtaaatgggt caagacagat    780
tctgaatata tagtcctaga aatttga                                        807

<210> SEQ ID NO 2
<211> LENGTH: 268
<212> TYPE: PRT
<213> ORGANISM: Prunus persica

<400> SEQUENCE: 2

Met Lys Leu Phe Gly Trp Met Gln Asn Lys Leu Asn Gly Lys Gln Gly
 1               5                  10                  15

Asn Lys Lys Pro Asn Thr Val Pro Ile Thr Thr His Pro Ala Lys Gln
            20                  25                  30

Glu Pro Arg Glu Glu Phe Ser Asp Trp Pro His Gly Leu Leu Ala Ile
        35                  40                  45

Gly Thr Phe Gly Asn Asn Asp Leu Lys Glu Asn Ala Ala Glu Ser Gln
    50                  55                  60

Asp Ile Gln Glu Asp Pro Thr Ser Ser Glu Glu Ile Leu Asp Asn Phe
65                  70                  75                  80

Thr Pro Glu Glu Val Gly Lys Leu His Lys Glu Leu Thr Lys Leu Leu
                85                  90                  95
```

```
Thr Arg Lys Pro Asn Ile Glu Lys Glu Ile Ala Asp Leu Pro Leu Asp
            100                 105                 110

Arg Phe Leu Asn Cys Pro Ser Ser Leu Glu Val Asp Arg Asn Ser
        115                 120                 125

Asn Ala Leu Cys Ser Asp Ser Ala Asp Asp His Lys Asp Glu Asp Ile
        130                 135                 140

Glu Lys Thr Ile Ser Val Ile Leu Gly Arg Cys Lys Glu Ile Cys Gly
145                 150                 155                 160

Asp Lys Asn Lys Lys Ala Ile Gly Lys Lys Ser Ile Ser Phe Leu Leu
                165                 170                 175

Lys Lys Met Phe Val Cys Arg Ser Gly Phe Ala Pro Gln Pro Ser Leu
            180                 185                 190

Arg Asp Thr Leu Gln Glu Ser Arg Met Glu Lys Leu Leu Arg Val Met
            195                 200                 205

Leu Asn Lys Lys Ile Ile Asn Pro Gln Gly Ser Ser Arg Ala Ala Ser
210                 215                 220

Met Lys Lys Tyr Leu Glu Asp Arg Gln Ile Pro Thr Lys Lys Glu Ser
225                 230                 235                 240

Asn Thr Glu Asp Asp Thr Lys Glu Lys Ile Asn Asn Gly Cys Lys Trp
                245                 250                 255

Val Lys Thr Asp Ser Glu Tyr Ile Val Leu Glu Ile
            260                 265

<210> SEQ ID NO 3
<211> LENGTH: 14000
<212> TYPE: DNA
<213> ORGANISM: Prunus persica

<400> SEQUENCE: 3
ccgggctggt tgccctcgcc gctgggctgg cggccgtcta tggccctgca acgcgccag      60 aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgaggggc agagtgctga cagatgaggg gcgcacctat    420
tgacatttga ggggctgtcc acaggcagaa aatccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgccccc     600 cttctcgaac cctcccggcc cgctaacgcg ggcctcccat cccccaggg gctgcgcccc     660 tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gaccttttaca gaattactct atgaagcgcc atatttaaaa agctaccaag   1080
acgaagagga tgaagaggat gaggaggcag attgccttga atatattgac aatactgata   1140
```

```
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataaccct atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttacata tgcggtgtga ataccgcac agatgcgtaa ggagaaaata   1800
ccgcatcagg cgctcttccg cttcctcgct cactgactcg ctgcgctcgg tcgttcggct   1860
gcggcgagcg gtatcagctc actcaaaggc ggtaatacgg ttatccacag aatcagggga   1920
taacgcagga aagaacatgt gagcaaaagg ccagcaaaag gccaggaacc gtaaaaaggc   1980
cgcgttgctg gcgtttttcc ataggctccg ccccctgac gagcatcaca aaaatcgacg   2040
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gttttttaag tgacgtaaaa tcgtgttgag   2400
gccaacgccc ataatgcggg ctgttgcccg gcatccaacg ccattcatgg ccatatcaat   2460
gattttctgg tgcgtaccgg ttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa ataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg gaagaagac   3360
actccattta aagatccgcg cgagctgtat gattttttaa agacggaaaa gcccgaagag   3420
gaacttgtct tttcccacgg cgacctggga gacagcaaca tctttgtgaa agatggcaaa   3480
```

-continued

```
gtaagtggct ttattgatct tgggagaagc ggcagggcgg acaagtggta tgacattgcc    3540
ttctgcgtcc ggtcgatcag ggaggatatc ggggaagaac agtatgtcga gctattttt     3600 gacttactgg ggatcaagcc tgattgggag aaaataaaat attatatttt actggatgaa    3660
ttgttttagt acctagatgt ggcgcaacga tgccggcgac aagcaggagc gcaccgactt    3720
cttccgcatc aagtgttttg gctctcaggc cgaggcccac ggcaagtatt tgggcaaggg    3780
gtcgctggta ttcgtgcagg gcaagattcg gaataccaag tacgagaagg acggccagac    3840
ggtctacggg accgacttca ttgccgataa ggtggattat ctggacacca aggcaccagg    3900
cgggtcaaat caggaataag ggcacattgc cccggcgtga gtcggggcaa tcccgcaagg    3960
agggtgaatg aatcggacgt ttgaccggaa ggcatacagg caagaactga tcgacgcggg    4020
gttttccgcc gaggatgccg aaaccatcgc aagccgcacc gtcatgcgtg cgccccgcga    4080
aaccttccag tccgtcggct cgatggtcca gcaagctacg gccaagatcg agcgcgacag    4140
cgtgcaactg gctcccctg ccctgcccgc gccatcggcc gccgtggagc gttcgcgtcg     4200
tctcgaacag gaggcggcag gtttggcgaa gtcgatgacc atcgacacgc gaggaactat    4260
gacgaccaag aagcgaaaaa ccgccggcga ggacctggca aaacaggtca gcgaggccaa    4320
gcaggccgcg ttgctgaaac acacgaagca gcagatcaag gaaatgcagc tttccttgtt    4380
cgatattgcg ccgtggccgg acacgatgcg agcgatgcca aacgacacgg cccgctctgc    4440
cctgttcacc acgcgcaaca agaaaatccc gcgcgaggcg ctgcaaaaca aggtcatttt    4500
ccacgtcaac aaggacgtga agatcaccta caccggcgtc gagctgcggg ccgacgatga    4560
cgaactggtg tggcagcagg tgttggagta cgcgaagcgc accctatcg gcgagccgat     4620 caccttcacg ttctacgagc tttgccagga cctgggctgg tcgatcaatg gccggtatta    4680
cacgaaggcc gaggaatgcc tgtcgcgcct acaggcgacg gcgatgggct tcacgtccga    4740
ccgcgttggg cacctggaat cggtgtcgct gctgcaccgc ttccgcgtcc tggaccgtgg    4800
caagaaaacg tcccgttgcc aggtcctgat cgacgaggaa atcgtcgtgc tgtttgctgg    4860
cgaccactac acgaaattca tatgggagaa gtaccgcaag ctgtcgccga cggcccgacg    4920
gatgttcgac tatttcagct cgcaccggga gccgtacccg ctcaagctgg aaaccttccg    4980
cctcatgtgc ggatcggatt ccacccgcgt gaagaagtgg cgcgagcagg tcggcgaagc    5040
ctgcgaagag ttgcgaggca gcggcctggt ggaacacgcc tgggtcaatg atgacctggt    5100
gcattgcaaa cgctagggcc ttgtggggtc agttccggct gggggttcag cagccagcgc    5160
tttactggca tttcaggaac aagcgggcac tgctcgacgc acttgcttcg ctcagtatcg    5220
ctcgggacgc acggcgcgct ctacgaactg ccgataaaca gaggattaaa attgacaatt    5280
gtgattaagg ctcagattcg acggcttgga gcggccgacg tgcaggattt ccgcgagatc    5340
cgattgtcgg ccctgaagaa agctccagag atgttcgggt ccgtttacga gcacgaggag    5400
aaaaagccca tggaggcgtt cgctgaacgg ttgcgagatg ccgtggcatt cggcgcctac    5460
atcgacggcg agatcattgg gctgtcggtc ttcaaacagg aggacggccc caaggacgct    5520
cacaaggcgc atctgtccgg cgttttcgtg gagcccgaac agcgaggccg aggggtcgcc    5580
ggtatgctgc tgcgggcgtt gccggcgggt ttattgctcg tgatgatcgt ccgacagatt    5640
ccaacgggaa tctggtggat gcgcatcttc atcctcggcg cacttaatat ttcgctattc    5700
tggagcttgt tgtttatttc ggtctaccgc ctgccgggcg gggtcgcggc gacggtaggc    5760
gctgtgcagc cgctgatggt cgtgttcatc tctgccgctc tgctaggtag cccgatacga    5820
ttgatggcgg tcctgggggc tatttgcgga actgcgggcg tggcgctgtt ggtgttgaca    5880
```

```
ccaaacgcag cgctagatcc tgtcggcgtc gcagcggggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggaaccct gtggttggca tgcacataca   6240
aatggacgaa cggataaacc ttttcacgcc ctttttaaata tccgattatt ctaataaacg   6300
ctcttttctc ttagggccgg ccaccctgat aaatgcttca ataatattga aaaggaaga    6360
gtatgagtat tcaacatttc cgtgtcgccc ttattccctt ttttgcggca ttttgccttc   6420
ctgtttttgc tcacccagaa acgctggtga agtaaaaga tgctgaagat cagttgggtg    6480
cacgagtggg ttacatcgaa ctggatctca acagcggtaa gatccttgag agttttcgcc   6540
ccgaagaacg ttttccaatg atgagcactt ttaaagttct gctatgtggc gcggtattat   6600
cccgtattga cgccgggcaa gagcaactcg gtcgccgcat acactattct cagaatgact   6660
tggttgagta ctcaccagtc acagaaaagc atcttacgga tggcatgaca gtaagagaat   6720
tatgcagtgc tgccataacc atgagtgata acactgcggc caacttactt ctgacaacga   6780
tcggaggacc gaaggagcta accgcttttt tgcacaacat gggggatcat gtaactcgcc   6840
ttgatcgttg ggaaccggag ctgaatgaag ccataccaaa cgacgagcgt gacaccacga   6900
tgcctgtagc aatggcaaca acgttgcgca aactattaac tggcgaacta cttactctag   6960
cttcccggca caattaata gactggatgg aggcggataa agttgcagga ccacttctgc    7020
gctcggccct tccggctggc tggtttattg ctgataaatc tggagccggt gagcgtgggt   7080
ctcgcggtat cattgcagca ctggggccag atggtaagcc ctcccgtatc gtagttatct   7140
acacgacggg gagtcaggca actatggatg aacgaaatag acagatcgct gagataggtg   7200
cctcactgat taagcattgg taaaaaacgc gtatgccggc gtttacccgc caatatatcc   7260
tgtcagcggc cgctaactag ttaggcgcgc cactagagcc aagctgatct cctttgcccc   7320
ggagatcacc atggacgact ttctctatct ctacgatcta ggaagaaagt tcgacggaga   7380
aggtgacgat accatgttca ccaccgataa tgagaagatt agcctcttca atttcagaaa   7440
gaatgctgac ccacagatgg ttagagaggc ctacgcggca ggtctcatca agacgatcta   7500
cccgagtaat aatctccagg agatcaaata ccttcccaag aaggttaaag atgcagtcaa   7560
aagattcagg actaactgca tcaagaacac agagaaagat atatttctca agatcagaag   7620
tactattcca gtatggacga ttcaaggctt gcttcataaa ccaaggcaag taatagagat   7680
tggagtctct aagaaagtag ttcctactga atcaaaggcc atggagtcaa aaattcagat   7740
cgaggatcta acagaactcg ccgtgaagac tggcgaacag ttcatacaga gtcttttacg   7800
actcaatgac aagaagaaaa tcttcgtcaa catggtggag cacgcactc tcgtctactc     7860
caagaatatc aaagatacag tctcagaaga ccaagggct attgagactt tcaacaaag    7920
ggtaatatcg gaaacctcc tcggattcca ttgcccagct atctgtcact tcatcaaaag    7980
gacagtagaa aaggaaggtg gcacctacaa atgccatcat tgcgataaag gaaaggctat    8040
cgttcaagat gcctctgccg acagtggtcc caaagatgga ccccacccca cgaggagcat    8100
cgtggaaaaa gaagacgttc caaccacgtc ttcaaagcaa gtggattgat gtgatatctc    8160
cactgacgta agggatgacg cacaatccca ctatccttcg caagaccctt cctctatata    8220
```

-continued

```
aggaagttca tttcatttgg agaggactcc ggtatttta caacaatacc acaacaaaac    8280
aaacaacaaa caacattaca atttactatt ctagtcgagt cgacatgaag cttttggtt    8340 ggatgcaaaa taagcttaat ggaaagcagg ggaacaagaa accaaataca gttcctatta    8400
ctactcatcc tgcaaaacaa gagcctcgtg aagaattcag tgactggcct catggattac    8460
tagcaattgg aacttttgga acaatgatt tgaaagaaaa tgcagctgaa agccaagata    8520
ttcaggaaga tccaacttca tcagaagaaa tactagataa tttcactcct gaagaggttg    8580
gcaaattaca taaagagtta acaaagctct taacgcgaaa accaaacatc gaaaggaaa     8640 tcgcagatct tccattggac agatttctaa actgcccatc aagcttggag gttgatcgga    8700
gaaacagcaa tgcactttgc tccgattcag cagatgatca caaggatgaa acattgaga     8760 agactattag tgtcatactt ggtagatgca aagaaatttg tggagataag aataagaagg    8820
caattgggaa gaaatctatt tcttttcttc tcaagaagat gtttgtttgc agaagtggat    8880
ttgcaccaca accaagtttg agagatacac ttcaagagtc aagaatggag aagcttttga    8940
gggtaatgct taacaagaag atcatcaatc cgcaaggatc ttctcgagca gcatcgatga    9000
agaaatacct ggaggataga cagattccaa caaagaagga agtaacact gaagatgata    9060 caaaagagaa aattaataat ggatgtaaat gggtcaagac agattctgaa tatatagtcc    9120
tagaaatttg aggatccatt ctagatagcg atcgcatacc ggtatcccgg gacctgcagg    9180
ttcaattgta gtttaaactg attttaatgt ttagcaaatg tcttatcagt tttctctttt    9240
tgtcgaacgg taatttagag tttttttgc tatatggatt ttcgttttg atgtatgtga     9300 caaccctcgg gattgttgat ttatttcaaa actaagagtt tttgtcttat tgttctcgtc    9360
tattttggat atcaatctta gttttatatc ttttctagtt ctctacgtgt taaatgttca    9420
acacactagc aatttggcct gccagcgtat ggattatgga actatcaagt gtgtgggatc    9480
gataaatatg cttctcagga atttgagatt ttacagtctt tatgctcatt gggttgagta    9540
taatatagta aaaaaatagt aaatttaagc aataatgtta ggtgctatgt gtctgtcgag    9600
actattctcg agatcatatg ataatcgata tttaattaaa tcacgtgatt acgtatagta    9660
tacatgatct agtaacatag atgacaccgc gcgcgataat ttatcctagt ttgcgcgcta    9720
tattttgttt tctatcgcgt attaaatgta taattgcggg actctaatca taaaaaccca    9780
tctcataaat aacgtcatgc attacatgtt aattattaca tgcttaacgt aattcaacag    9840
aaattatatg ataatcatcg caagaccggc aacaggattc aatcttaaga aactttattg    9900
ccaaatgttt gaacgatctc agaagaactc gtcaagaagg cgatagaagg cgatgcgctg    9960
cgaatcggga gcggcgatac cgtaaagcac gaggaagcgg tcagcccatt cgccgccaag   10020
ctcttcagca atatcacggg tagccaacgc tatgtcctga tagcggtccg ccacacccag   10080
ccggccacag tcgatgaatc cagaaaagcg gccattttcc accatgatat tcggcaagca   10140
ggcatcgcca tgggtcacga cgagatcatc gccgtcgggc atgcgcgcct tgagcctggc   10200
gaacagttcg gctggcgcga gcccctgatg ctcttcgtcc agatcatcct gatcgacaag   10260
accggcttcc atccgagtac gtgctcgctc gatgcgatgt ttcgcttggt ggtcgaatgg   10320
gcaggtagcc ggatcaagcg tatgcagccg ccgcattgca tcagccatga tggatacttt   10380
ctcggcagga gcaaggtgag atgacaggag atcctgcccc ggcacttcgc ccaatagcag   10440
ccagtccctt cccgcttcag tgacaacgtc gagcacagct gcgcaaggaa cgcccgtcgt   10500
ggccagccac gatagccgcg ctgcctcgtc ctgcagttca ttcagggcac cggacaggtc   10560
ggtcttgaca aaaagaaccg ggcgcccctg cgctgacagc cggaacacgg cggcatcaga   10620
```

```
gcagccgatt gtctgttgtg cccagtcata gccgaatagc ctctccaccc aagcggccgg   10680
agaacctgcg tgcaatccat cttgttcaat cattgcagat tatttggatt gagagtgaat   10740
atgagactct aattggatac cgaggggaat ttatgaacg tcagtggagc attttttgaca   10800 agaaatattt gctagctgat agtgacctta ggcgactttt gaacgcgcaa taatggtttc   10860
tgacgtatgt gcttagctca ttaaactcca gaaacccgcg gctgagtggc tccttcaacg   10920
ttgcggttct gtcagttcca aacgtaaaac ggcttgtccc gcgtcatcgg cggggggtcat  10980 aacgtgactc ccttaattct ccgctcatga tcagattgtc gtttcccgcc ttcagtttaa   11040
actatcagtg ttggccggcg cctaggttcg tacgattcgc gaatggtacc atatttaaat   11100
gtttacacca caatatatcc tgccagggcc catttcgaaa aaggccggcc ccagccagcc   11160
aacagctccc cgaccggcag ctcggcacaa aatcaccact cgataccagg cagcccatcag   11220 tccgggacgg cgtcagcggg agagccgttg taaggcggca gactttgctc atgttaccga   11280
tgctattcgg aagaacggca actaagctgc cgggtttgaa acacggatga tctcgcggag   11340
ggtagcatgt tgattgtaac gatgacagag cgttgctgcc tgtgatcaaa tatcatctcc   11400
ctcgcagaga tccgaattat cagccttctt attcatttct cgcttaaccg tgacaggctg   11460
tcgatcttga gaactatgcc gacataatag gaaatcgctg gataaagccg ctgaggaagc   11520
tgagtggcgc tatttctta gaagtgaacg ttgaccatat caactcccct atccattgct   11580
caccgaatgg tacaggtcgg ggacccgaag ttccgactgt cggcctgatg catccccggc   11640
tgatcgaccc cagatctggc gccggccagc gagacgagca agattggccg ccgcccgaaa   11700
cgatccgaca gcgcgcccag cacaggtgcg caggcaaatt gcaccaacgc atacagcgcc   11760
agcagaatgc catagtgggc ggtgacgtcg ttcgagtgaa ccagatcgcg caggaggccc   11820
ggcagcaccg gcataatcag gccgatgccg acagcgtcga gcgcgacagt gctcagaatt   11880
acgatcaggg gtatgttggg tttcacgtct ggcctccgga ccagcctccg ctggtccgat   11940
tgaacgcgcg gattctttat cactgataag ttggtggaca tattatgttt atcagtgata   12000
aagtgtcaag catgacaaag ttgcagccga atacagtgat ccgtgccgcc ctggacctgt   12060
tgaacgaggt cggcgtagac ggtctgacga cacgcaaact ggcggaacgg ttgggggttc   12120
agcagccggc gctttactgg cacttcagga acaagcgggc gctgctcgac gcactggccg   12180
aagccatgct ggcggagaat catacgcatt cggtgccgag agccgacgac gactggcgct   12240
catttctgat cgggaatgcc cgcagcttca ggcaggcgct gctcgcctac cgcgatggcg   12300
cgcgcatcca tgccggcacg cgaccgggcg caccgcagat ggaaacggcc gacgcgcagc   12360
ttcgcttcct ctgcgaggcg ggttttttcgg ccggggacgc cgtcaatgcg ctgatgacaa   12420
tcagctactt cactgttggg gccgtgcttg aggagcagge cggcgacagc gatgccggcg   12480
agcgcggcgg caccgttgaa caggctccgc tctcgccgct gttgcgggcc gcgatagacg   12540
ccttcgacga agccggtccg gacgcagcgt tcgagcaggg actcgcggtg attgtcgatg   12600
gattggcgaa aaggaggctc gttgtcagga acgttgaagg accgagaaag ggtgacgatt   12660
gatcaggacc gctgccggag cgcaacccac tcactacagc agagccatgt agacaacatc   12720 ccctcccct ttccaccgcg tcagacgccc gtagcagccc gctacgggct ttttcatgcc   12780
ctgccctagc gtccaagcct cacggccgcg ctcggcctct ctggcggcct tctggcgctc   12840
ttccgcttcc tcgctcactg actcgctgcg ctcggtcgtt cggctgcggc gagcggtatc   12900
agctcactca aaggcggtaa tacggttatc cacagaatca ggggataacg caggaaagaa   12960
```

```
catgtgagca aaaggccagc aaaaggccag gaaccgtaaa aaggccgcgt tgctggcgtt    13020
tttccatagg ctccgccccc ctgacgagca tcacaaaaat cgacgctcaa gtcagaggtg    13080
gcgaaacccg acaggactat aaagatacca ggcgtttccc cctggaagct ccctcgtgcg    13140
ctctcctgtt ccgaccctgc cgcttaccgg atacctgtcc gcctttctcc cttcgggaag    13200
cgtggcgctt tccgctgca taaccctgct tcggggtcat tatagcgatt ttttcggtat    13260
atccatcctt tttcgcacga tatacaggat tttgccaaag ggttcgtgta gactttcctt    13320
ggtgtatcca acggcgtcag ccgggcagga taggtgaagt aggcccaccc gcgagcgggt    13380
gttccttctt cactgtccct tattcgcacc tggcggtgct caacgggaat cctgctctgc    13440
gaggctggcc ggctaccgcc ggcgtaacag atgagggcaa gcggatggct gatgaaacca    13500
agccaaccag gaagggcagc ccacctatca aggtgtactg ccttccagac gaacgaagag    13560
cgattgagga aaaggcggcg gcggccggca tgagcctgtc ggcctacctg ctggccgtcg    13620
gccagggcta caaaatcacg ggcgtcgtgg actatgagca cgtccgcgag ctggcccgca    13680
tcaatggcga cctgggccgc ctgggcgcc tgctgaaact ctggctcacc gacgacccgc    13740
gcacggcgcg gttcggtgat gccacgatcc tcgccctgct ggcgaagatc gaagagaagc    13800
aggacgagct tggcaaggtc atgatgggcg tggtccgccc gagggcagag ccatgacttt    13860
tttagccgct aaaacggccg gggggtgcgc gtgattgcca agcacgtccc catgcgctcc    13920
atcaagaaga gcgacttcgc ggagctggtg aagtacatca ccgacgagca aggcaagacc    13980
gagcgccttt gcgacgctca                                                14000
```

<210> SEQ ID NO 4
<211> LENGTH: 7
<212> TYPE: PRT
<213> ORGANISM: Oryza sativa

<400> SEQUENCE: 4

Lys Trp Val Lys Thr Asp Ser
1               5

<210> SEQ ID NO 5
<211> LENGTH: 5
<212> TYPE: PRT
<213> ORGANISM: Oryza sativa

<400> SEQUENCE: 5

Ile Val Leu Glu Ile
1               5

<210> SEQ ID NO 6
<211> LENGTH: 302
<212> TYPE: PRT
<213> ORGANISM: Prunus persica

<400> SEQUENCE: 6

Met Lys Ile Phe Asn Trp Val His Lys Arg Leu His Gln Arg Val Val
1               5                   10                  15

Lys Asp Gly Phe Ala Gly Asn Val Lys Lys Ser Glu Leu Glu Thr Asn
            20                  25                  30

Asp Lys Asp Thr Gln Ala Phe Leu Lys Gln Val Gly Leu Val Asn Val
        35                  40                  45

Asp Gly Leu Asp Gly Trp Arg Asp Gly Ile Leu Thr Ile Gly Thr Phe
    50                  55                  60

Gly Phe Asp Pro Leu Lys Pro Ser Thr His Gln Asn Glu Tyr Phe Val

```
                65                  70                  75                  80
Leu Glu Ser Glu Glu Asp Asp Gln Ser His Gly Phe Ser His Ser
                    85                  90                  95

Gly Asn Asp Asp Asp Asp Asp Glu His Tyr Asp His Ser Val
                100                 105                 110

Glu Asp Glu Glu Leu Asn Pro Leu Met Phe Thr Thr Phe Glu His Ser
            115                 120                 125

Phe Glu Asp Ile Gly Ser Asn Phe Asp Ala Ile Val Gln Lys Pro Ala
130                 135                 140

Asp Val Ile Leu Thr Val Asp Gly Val Pro Leu Thr Pro Phe Glu Gly
145                 150                 155                 160

Ser Ser Glu Ile Ser Thr Lys Pro Asp Gln Ser Ala Asn Asp Gln Ser
                165                 170                 175

Lys Asn Lys Lys Gly Gln Arg Ile Thr Leu Ala Asp Leu Phe Gln Ala
            180                 185                 190

Asp Val Pro Asp Val Gly Gln Leu Lys Leu Asp Ser Gly Lys Val Gln
        195                 200                 205

Pro Glu Met Glu Lys Lys Met Asn Ala Arg Thr Arg Ser Gly Leu Ala
    210                 215                 220

Phe Ala Lys Lys Leu Ile Pro Arg Val Lys Asp Ser Ser Pro Ile
225                 230                 235                 240

Lys Asn Met Gln Arg Leu Met Arg Met Leu Lys Arg Lys Ile His
                245                 250                 255

Pro Ala Glu Leu Glu Val Lys Ile His Lys Ser Asp Gly Gln Lys Gln
            260                 265                 270

Pro Ser Ala Val Glu Leu Ile Ser Asn Val Glu Asn Asp Ala Tyr Glu
        275                 280                 285

Ser Val Ser Leu Leu Pro Ile Gln Gly Ala Pro Cys Val His
    290                 295                 300

<210> SEQ ID NO 7
<211> LENGTH: 281
<212> TYPE: PRT
<213> ORGANISM: Arabidopsis thaliana

<400> SEQUENCE: 7

Met Thr Ile Phe Asn Trp Val Gln Lys Lys Leu His Gln Asn Val Ile
1               5                   10                  15

Lys Asp Gly Val Arg Lys Asn Glu Lys Lys Arg Asn Glu Gly Ile
            20                  25                  30

Ser Glu Ile Glu Lys Asn Thr Lys Ala Ile Leu Asp Gln Val Gly Leu
        35                  40                  45

Val Asp Ala Leu Asp Asn Trp Phe Asp Gly Val Leu Thr Ile Gly Thr
    50                  55                  60

Phe Gly Phe Asp Thr Leu Asn Phe Lys Glu Glu Asp Glu Met Asp Asp
65                  70                  75                  80

Asp Glu Cys Gly Ser Gly Asp Leu Asp Tyr Val Val Ile Asp Gly Ser
                85                  90                  95

Ile Ile Lys Asn Val Asp Gln Glu Ser Asp Pro Leu Ile Ser Val Glu
            100                 105                 110

Asn Lys Phe Tyr Asp His His Glu Asp Val Gly Asn Leu Tyr Val Gln
        115                 120                 125

Ala Asp Thr Asp His Phe Gly Ser Ile Lys Thr Ala Glu Thr Pro Ala
    130                 135                 140
```

```
Val Thr Ala Ala Ala Glu Ala Glu Ile Glu Pro Gln Lys Lys Arg Thr
145                 150                 155                 160

Thr Leu Ala Glu Leu Phe Met Glu Asp His Asp Lys Gly Tyr Asp Thr
                165                 170                 175

Trp His Cys Lys Lys Pro Asn Asn Pro Asn Leu Asp Gly Glu Glu Val
            180                 185                 190

Lys Tyr Tyr Lys Gln Asn Gly Ser Lys Leu Ser Lys Arg Phe Ser Phe
        195                 200                 205

Val Lys Lys Lys Leu Val Met Ser Lys Ser Lys Glu Glu Asn Asp
    210                 215                 220

Leu Arg Pro Ile Lys Lys Met Arg Gln Met Ile Lys Arg Met Leu Lys
225                 230                 235                 240

Lys Lys Ile His Pro Asp Val Asp Ala Thr Lys Ala Leu Lys Lys Asp
                245                 250                 255

Val Pro Tyr Lys Pro Thr Arg Asn Cys Glu Ala Leu Glu Ser His Tyr
                260                 265                 270

Leu Leu Lys Ile Gln Asp Cys Val Ala
            275                 280

<210> SEQ ID NO 8
<211> LENGTH: 259
<212> TYPE: PRT
<213> ORGANISM: Oryza sativa

<400> SEQUENCE: 8

Met Ala Leu Lys Val Phe Asn Trp Leu Asn Arg Lys Lys His Ser Asn
1               5                   10                  15

Val Glu Tyr Cys Thr Ile Asn Glu Asn Lys Ala Met Glu Glu Lys Glu
                20                  25                  30

Asp Ser Leu Arg Ala Ser Val Thr Glu Gln Asp Thr Glu Ala Leu Leu
            35                  40                  45

Leu Arg Asp Val Leu Ile Asn Gly Ile Leu Ala Ile Gly Thr Leu Gly
        50                  55                  60

His Asn Val Asn Ser Leu Cys Pro Glu Ser Cys Ile Glu Gln Asp Glu
65                  70                  75                  80

Pro Ile Ile Met Cys Asp Glu Lys Val Glu Gln Lys Cys Glu Glu
                85                  90                  95

Glu Lys Ala Glu Ala Lys Gln Asp Thr Pro Val Thr Ala Pro Ser Glu
            100                 105                 110

Pro Ala Ser Ala Leu Glu Pro Ala Lys Met His Ser Ser Met Lys
        115                 120                 125

Glu Asp Asn Phe Met Cys Phe Val Lys Glu Glu Ile Leu Met His Gly
    130                 135                 140

Met Glu Val Glu Asp Val Pro Asn Ile Gln Glu Arg Pro Leu Leu Met
145                 150                 155                 160

Leu Glu Lys Val Glu Lys Val Arg Thr Thr Leu Ala Asp Leu Phe Ala
                165                 170                 175

Ala Glu Ala Phe Ser Ser Ser Asp Ala Glu Asp Lys Cys Tyr Pro Lys
            180                 185                 190

Ile Val Ile Val Ala Gly Ala Ser Thr Ser Lys Pro Thr Ser Cys Met
        195                 200                 205

Glu Lys Met His His Lys Lys Pro Thr Lys Pro Thr Ser Lys Pro Leu
    210                 215                 220

Lys Ala Thr Arg Lys Leu Ser Arg Val Met Arg Lys Met Leu Gly Lys
225                 230                 235                 240
```

```
Lys Ile His Pro Glu Gln Leu Asn Gly Arg Ser Asn Ala Glu Gly Pro
            245                 250                 255

Val Thr Ala

<210> SEQ ID NO 9
<211> LENGTH: 221
<212> TYPE: PRT
<213> ORGANISM: Oryza sativa

<400> SEQUENCE: 9

Met Lys Ile Phe Ser Trp Val Ala Asn Lys Ile Ser Gly Lys Gln Glu
1               5                   10                  15

Ala Asn Arg Phe Pro Ala Asn Ser Ser Ala Pro Tyr Arg Ala Asn Val
            20                  25                  30

Ser Asp Cys Arg Lys Asp Glu Phe Ser Asp Trp Pro Gln Ser Leu Leu
        35                  40                  45

Ala Ile Gly Thr Phe Gly Asn Lys Gln Ile Glu Glu Val Ala Gln Val
    50                  55                  60

Glu Asn Ser Ser Asp Asn Val Gln Ser Val Gln Asp Thr Val Lys Phe
65                  70                  75                  80

Thr Glu Glu Glu Val Asp Lys Ile Arg Lys Glu Phe Glu Thr Leu Leu
                85                  90                  95

Ala Ile Lys Asp Gln Ala Glu Ala Gln Arg Ser His Asp Asp Asp Gln
            100                 105                 110

Val Gly Leu Gln Lys Arg Ala Asp Gly Glu Asp Asn Glu Lys His Ile
        115                 120                 125

Arg Gln Leu Ile Asn Lys Arg Ile Ile Val Ser Lys Ser Lys Asn Ser
    130                 135                 140

Leu Gly Lys Lys Gly Asn Thr Leu Lys Pro Arg Ser Val Ala Ser Leu
145                 150                 155                 160

Leu Lys Leu Phe Met Cys Lys Gly Gly Phe Thr Ser Val Val Pro Glu
                165                 170                 175

Pro Arg Asn Thr Phe Pro Gln Ser Arg Met Glu Lys Leu Leu Lys Ala
            180                 185                 190

Ile Leu Gln Lys Lys Ile Leu Arg Asp Leu Asp Asp Gly Ala Lys
        195                 200                 205

Trp Val Lys Thr Asp Ser Glu Tyr Ile Val Leu Glu Met
    210                 215                 220

<210> SEQ ID NO 10
<211> LENGTH: 177
<212> TYPE: PRT
<213> ORGANISM: Arabidopsis thaliana

<400> SEQUENCE: 10

Met Lys Ile Phe Ser Trp Val Gln Arg Lys Leu Ser Gly Lys Lys Arg
1               5                   10                  15

Val Pro Thr Ser Asp Ser Ser Gln Glu Pro Ser Pro Pro Leu Ser
            20                  25                  30

Lys Glu Val Gln Gly Leu Pro Gln Asp Glu Glu Thr Phe Leu Ala Ile
        35                  40                  45

Gly Thr Leu Gly Asn Asn Ile Phe Pro Lys Gln Glu Glu Glu Glu
    50                  55                  60

Glu Thr Asp Ser Ser Lys Asp Ile Thr Pro Val Asn Thr Asp Val Thr
65                  70                  75                  80
```

```
Ile Gly Lys Lys Lys Ser Leu Ser Phe Leu Lys Lys Met Phe Val
                85                  90                  95

Cys Thr Ser Gly Phe Lys Thr Pro Pro Leu Leu Asp Leu Ser Arg
            100                 105                 110

Gly Asp Ser Leu His Asn Thr Arg Met Glu Lys Met Leu Arg Thr Ile
            115                 120                 125

Leu Asn Lys Lys Ile His Pro Gln Arg Ser Asn Ser Ile Ala Lys Lys
    130                 135                 140

Tyr Leu Glu Ser Asn His Lys Ile Met Asp Glu Ala Arg Ser Ser Val
145                 150                 155                 160

Asp Ala Asn Lys Trp Val Lys Thr Asp Ser Glu Tyr Ile Val Leu Glu
                165                 170                 175

Met
```

<210> SEQ ID NO 11
<211> LENGTH: 264
<212> TYPE: PRT
<213> ORGANISM: Prunus persica

<400> SEQUENCE: 11

```
Met Gln Ser Lys Leu Thr Gly Lys Thr Gln Ile Lys Lys Pro Ser Ser
1               5                   10                  15

Lys Val Phe Asp Asp Lys Val Gln Lys Pro Pro Lys Glu Glu Val
            20                  25                  30

Asn Glu Trp Pro His Gly Leu Leu Thr Ile Gly Thr Leu Gly Asn Ser
                35                  40                  45

Asp Leu Lys Glu Asp Gln Gln Ser Asn Pro Pro Ser Pro Lys Asn
    50                  55                  60

His Pro His Gly Phe Thr Pro Glu Glu Val Arg Asn Ile Gln Asn Glu
65                  70                  75                  80

Leu Asn Ser Tyr Leu Asn Glu Glu Ala Asp His Gln Ser Asn Ser Gly
                85                  90                  95

Thr Glu Leu Glu Lys Val Pro Asn Phe Leu Pro Leu Asp Lys Phe Leu
            100                 105                 110

Asn Arg Gln Ser Ser Leu Lys Ala Glu Arg Asn Gly Asn Asn Ala Asp
            115                 120                 125

Cys Asp Glu Pro Lys Glu Asn Gly Ser Arg Phe Gln Arg Ser Gly Asn
    130                 135                 140

Val Val Leu Ser Arg Gly Lys Asp Val Cys Leu Glu Asn Thr Asn Thr
145                 150                 155                 160

Ala Ile Gly Lys Lys Ser Leu Ser Phe Leu Lys Lys Val Cys Val
                165                 170                 175

Cys Arg Ser Gly Phe Ala Pro Ala Ala Ala Pro Gly Leu Arg Asp Pro
            180                 185                 190

Ile Leu Glu Ser Arg Met Glu Lys Ile Leu Lys Ala Ile Leu His Lys
    195                 200                 205

Lys Ile Tyr Pro Lys Ser Ser Ser Ala Ser Thr Met Ser Met Lys Lys
    210                 215                 220

Tyr Leu Glu Asn Gly His Asn Ile Ala Lys Ser Ala Asn Asp Glu Glu
225                 230                 235                 240

Ile Asn Ile Asp Lys Glu Asp Glu Gly Ser Lys Trp Val Lys Thr Asp
                245                 250                 255

Ser Glu Tyr Ile Val Leu Glu Ile
            260
```

<210> SEQ ID NO 12
<211> LENGTH: 268
<212> TYPE: PRT
<213> ORGANISM: Prunus persica

<400> SEQUENCE: 12

Met Lys Leu Phe Gly Trp Met Gln Asn Lys Leu Asn Gly Lys Gln Gly
1               5                   10                  15

Asn Lys Lys Pro Asn Thr Val Pro Ile Thr Thr His Pro Ala Lys Gln
            20                  25                  30

Glu Pro Arg Glu Glu Phe Ser Asp Trp Pro His Gly Leu Leu Ala Ile
        35                  40                  45

Gly Thr Phe Gly Asn Asn Asp Leu Lys Glu Asn Ala Ala Glu Ser Gln
    50                  55                  60

Asp Ile Gln Glu Asp Pro Thr Ser Ser Glu Glu Ile Leu Asp Asn Phe
65                  70                  75                  80

Thr Pro Glu Glu Val Gly Lys Leu His Lys Glu Leu Thr Lys Leu Leu
                85                  90                  95

Thr Arg Lys Pro Asn Ile Glu Lys Glu Ile Ala Asp Leu Pro Leu Asp
            100                 105                 110

Arg Phe Leu Asn Cys Pro Ser Ser Leu Glu Val Asp Arg Arg Asn Ser
        115                 120                 125

Asn Ala Leu Cys Ser Asp Ser Ala Asp Asp His Lys Asp Glu Asp Ile
    130                 135                 140

Glu Lys Thr Ile Ser Val Ile Leu Gly Arg Cys Lys Glu Ile Cys Gly
145                 150                 155                 160

Asp Lys Asn Lys Lys Ala Ile Gly Lys Lys Ser Ile Ser Phe Leu Leu
                165                 170                 175

Lys Lys Met Phe Val Cys Arg Ser Gly Phe Ala Pro Gln Pro Ser Leu
            180                 185                 190

Arg Asp Thr Leu Gln Glu Ser Arg Met Glu Lys Leu Leu Arg Val Met
        195                 200                 205

Leu Asn Lys Lys Ile Ile Asn Pro Gln Gly Ser Ser Arg Ala Ala Ser
    210                 215                 220

Met Lys Lys Tyr Leu Glu Asp Arg Gln Ile Pro Thr Lys Lys Glu Ser
225                 230                 235                 240

Asn Thr Glu Asp Asp Thr Lys Glu Lys Ile Asn Asn Gly Cys Lys Trp
                245                 250                 255

Val Lys Thr Asp Ser Glu Tyr Ile Val Leu Glu Ile
            260                 265

<210> SEQ ID NO 13
<211> LENGTH: 287
<212> TYPE: PRT
<213> ORGANISM: Arabidopsis thaliana

<400> SEQUENCE: 13

Met Lys Phe Phe Gly Trp Met Gln Asn Lys Leu His Gly Lys Gln Glu
1               5                   10                  15

Ile Thr His Arg Pro Ser Ile Ser Ser Ala Ser Ser His His Pro Arg
            20                  25                  30

Glu Glu Phe Asn Asp Trp Pro His Gly Leu Leu Ala Ile Gly Thr Phe
        35                  40                  45

Gly Asn Lys Lys Gln Thr Pro Gln Thr Leu Asp Gln Glu Val Ile Gln
    50                  55                  60

```
Glu Glu Thr Val Ser Asn Leu His Val Glu Gly Arg Gln Ala Gln Asp
 65                  70                  75                  80

Thr Asp Gln Glu Leu Ser Ser Asp Asp Leu Glu Glu Asp Phe Thr
                 85                  90                  95

Pro Glu Glu Val Gly Lys Leu Gln Lys Glu Leu Thr Lys Leu Leu Thr
                100                 105                 110

Arg Arg Ser Lys Lys Arg Lys Ser Asp Val Asn Arg Glu Leu Ala Asn
            115                 120                 125

Leu Pro Leu Asp Arg Phe Leu Asn Cys Pro Ser Ser Leu Glu Val Asp
130                 135                 140

Arg Arg Ile Ser Asn Ala Leu Cys Asp Glu Lys Glu Glu Asp Ile Glu
145                 150                 155                 160

Arg Thr Ile Ser Val Ile Leu Gly Arg Cys Lys Ala Ile Ser Thr Glu
                165                 170                 175

Ser Lys Asn Lys Thr Lys Lys Asn Leu Arg Asp Leu Ser Lys Thr Ser
            180                 185                 190

Val Ser His Leu Leu Lys Lys Met Phe Val Cys Thr Glu Gly Phe Ser
        195                 200                 205

Pro Val Pro Arg Pro Ile Leu Arg Asp Thr Phe Gln Glu Thr Arg Met
210                 215                 220

Glu Lys Leu Leu Arg Met Met Leu His Lys Lys Val Asn Thr Gln Ala
225                 230                 235                 240

Ser Ser Lys Gln Thr Ser Thr Lys Lys Tyr Leu Gln Asp Lys Gln Gln
                245                 250                 255

Leu Ser Leu Lys Asn Glu Glu Glu Gly Arg Ser Ser Asn Asp Gly
            260                 265                 270

Gly Lys Trp Val Lys Thr Asp Ser Asp Phe Ile Val Leu Glu Ile
        275                 280                 285

<210> SEQ ID NO 14
<211> LENGTH: 295
<212> TYPE: PRT
<213> ORGANISM: Arabidopsis thaliana

<400> SEQUENCE: 14

Met Lys Phe Phe Gly Trp Met Gln Asn Lys Leu Asn Gly Asp His Asn
1               5                   10                  15

Arg Thr Ser Thr Ser Ser Ala Ser Ser His His Val Lys Gln Glu Pro
            20                  25                  30

Arg Glu Glu Phe Ser Asp Trp Pro His Ala Leu Leu Ala Ile Gly Thr
        35                  40                  45

Phe Gly Thr Thr Ser Asn Ser Val Ser Glu Asn Glu Ser Lys Asn Val
50                  55                  60

His Glu Glu Ile Glu Ala Glu Lys Lys Cys Thr Ala Gln Ser Glu Gln
65                  70                  75                  80

Glu Glu Glu Pro Ser Ser Ser Val Asn Leu Glu Asp Phe Thr Pro Glu
                85                  90                  95

Glu Val Gly Lys Leu Gln Lys Glu Leu Met Lys Leu Leu Ser Arg Thr
            100                 105                 110

Lys Lys Arg Lys Ser Asp Val Asn Arg Glu Leu Met Lys Asn Leu Pro
        115                 120                 125

Leu Asp Arg Phe Leu Asn Cys Pro Ser Ser Leu Glu Val Asp Arg Arg
130                 135                 140

Ile Ser Asn Ala Leu Ser Ala Val Val Asp Ser Ser Glu Glu Asn Lys
145                 150                 155                 160
```

```
Glu Glu Asp Met Glu Arg Thr Ile Asn Val Ile Leu Gly Arg Cys Lys
            165                 170                 175

Glu Ile Ser Ile Glu Ser Lys Asn Asn Lys Lys Arg Asp Ile Ser
        180                 185                 190

Lys Asn Ser Val Ser Tyr Leu Phe Lys Lys Ile Phe Val Cys Ala Asp
            195                 200                 205

Gly Ile Ser Thr Ala Pro Ser Pro Ser Leu Arg Asp Thr Leu Gln Glu
            210                 215                 220

Ser Arg Met Glu Lys Leu Leu Lys Met Met Leu His Lys Lys Ile Asn
225                 230                 235                 240

Ala Gln Ala Ser Ser Lys Pro Thr Ser Leu Thr Thr Lys Arg Tyr Leu
                245                 250                 255

Gln Asp Lys Lys Gln Leu Ser Leu Lys Ser Glu Glu Glu Thr Ser
            260                 265                 270

Glu Arg Arg Ser Ser Ser Asp Gly Tyr Lys Trp Val Lys Thr Asp Ser
            275                 280                 285

Asp Phe Ile Val Leu Glu Ile
            290                 295

<210> SEQ ID NO 15
<211> LENGTH: 416
<212> TYPE: PRT
<213> ORGANISM: Oryza sativa

<400> SEQUENCE: 15

Met Lys Leu Leu Gly Trp Met His Arg Lys Leu Arg Ser Asn Asn Asp
1               5                   10                  15

Val Phe Lys Glu Phe Asn Thr Gly Gly Gly Ala Cys Asn Cys Ile
            20                  25                  30

Thr Gly Leu Ala Ser Pro Asp His Asp Asn Asp Tyr Phe Ser Gly Asp
        35                  40                  45

Asp Ala Ala His Ala Ser Pro Pro Val Thr Ala Gly Asp Leu Phe Thr
    50                  55                  60

Phe Gly Gly Ser Gly Leu Leu Thr Ile Gly Thr Leu Gly Ile Ala Ala
65                  70                  75                  80

Val Ala Ile Pro Ser Gly Gly Asp Asp Asp Tyr Asp Ile Asp Phe
                85                  90                  95

Glu Val Asp Ala Thr Ser Asp Asp Gly Gly Phe Thr Val Glu Asp
            100                 105                 110

Asp Asp Ala Asp Val Gly Gly Ala Val Thr Pro Thr Phe Thr Phe Pro
        115                 120                 125

Ala Ala Thr Ala Ala Glu Ala Val Val Ala Thr Val Glu Lys Ala Val
    130                 135                 140

Ala Ala Val Glu Ala Ile Ala Glu Lys Asp Asp Asp Thr Thr Thr Glu
145                 150                 155                 160

Asp Asp Leu Met Val Val Ser Ala Glu Leu Lys Val Leu Gly Gly
                165                 170                 175

Val Asp Val Ala Ser Ala Arg Val Ser Phe Ala Met Gly Gly Gly Val
            180                 185                 190

Asp Cys Pro Leu Gln Gly Phe Leu Phe Gly Ser Pro Val Ser Asp Val
        195                 200                 205

Glu Ser Arg Pro Glu Tyr Leu Gln Ala Pro Arg Asp Ser Ser Gly Ser
    210                 215                 220

Cys Gly Gly Gly Gly Arg Arg Thr Ser Leu Gly Glu Leu Phe Met Arg
```

-continued

```
                225                 230                 235                 240

Thr Arg Phe Ala Asp Glu Lys Val Ala Leu Val Ala Val Ala Glu Gly
                        245                 250                 255

Glu Asp Gly Val Ala Gly Asp Asp Gly Ala Ala Ala Gly Val Gly
                        260                 265                 270

Gly Asp Arg Ala Gly Lys Gly Gly Tyr Lys Thr Met Lys Lys Arg
                        275                 280                 285

Lys Val Lys Asp Glu Lys Gly Gly Gly Ala Ala Gly Gly Gly Met
                        290                 295                 300

Pro Ala Thr Val Thr Lys Ser Lys Phe Gln Lys Ile Leu Gln Ile Phe
        305                 310                 315                 320

His Arg Lys Val Tyr Pro Glu Asn Thr Leu Leu Thr Arg Asn Leu Thr
                        325                 330                 335

Lys Lys Ser Arg Asn Arg Gly Ala Thr Asp Asn Gly Gly Gly Ala Val
                        340                 345                 350

Ala Thr Gly Asp Pro Asp Gly Pro Leu Ala Ser Pro Val Leu Arg Cys
                        355                 360                 365

Arg Lys Asp His Pro Met Arg Gly Phe Gly Cys Cys Thr Asn Gly Ala
                        370                 375                 380

Phe Gly Ala Ser Ser Pro Gly Gly Asn Ala Glu Met Asn Gly Asn Lys
        385                 390                 395                 400

Ser Gly His Trp Ile Lys Thr Asp Ala Asp Tyr Leu Val Leu Glu Leu
                        405                 410                 415

<210> SEQ ID NO 16
<211> LENGTH: 358
<212> TYPE: PRT
<213> ORGANISM: Arabidopsis thaliana

<400> SEQUENCE: 16

Met Lys Phe Trp Gly Trp Met His His Lys Phe Arg Glu Asn Ser Lys
1               5                   10                  15

Glu Pro Leu Lys Asp Ala Ser Thr Gly Asn Ser Tyr Ser Ile Leu Ser
                20                  25                  30

Ala His Pro Ser Leu Asp Ser Gln Glu Val Tyr Pro Thr Ala Cys Ala
            35                  40                  45

Gly Ser Arg Tyr Asn Thr Gly Phe Arg Lys Gln Val Asn Leu Phe Gln
        50                  55                  60

Glu Ser Ser Phe Ala Gly Pro Lys Gln Tyr Thr Glu Glu Asp Phe Lys
65                  70                  75                  80

Asp Glu Arg Asn Ser Asp Phe Asp Gly Phe Leu Ala Ile Gly Thr
                85                  90                  95

Leu Gly Gly Glu Thr Leu Leu Asp Glu Gln Pro Ala Thr Pro Thr Phe
            100                 105                 110

Gly Met Ser Phe Glu Asp Pro Ala Ile Asp Asp Ala Asp Val Thr Glu
        115                 120                 125

Asn Asp Leu Lys Leu Ile Ser Asn Glu Leu Asp Lys Phe Leu Glu Ala
    130                 135                 140

Glu Ala Lys Glu Gly His His Gln Pro Ser Gly Arg Asn Ser Asp Thr
145                 150                 155                 160

Asn Thr Ile Ala Ser Thr Ile Glu Ala Ile Glu Gly Val Asp Asp Glu
                165                 170                 175

Glu Asp Asn Gln Pro Met Lys Phe Pro Leu Gln Glu Tyr Phe Phe Gly
            180                 185                 190
```

```
Ser Leu Ile Glu Leu Pro Glu Ser Lys Ile Ala Gly Lys Lys Asp Arg
            195                 200                 205

Ala Ser Leu Gly Glu Leu Phe Gln Ile Thr Glu Val Gln Asp Lys Gln
        210                 215                 220

Ser Glu Asn Ile Tyr Gly Lys Lys Lys Gln Pro Asn Ser Ala His
225                 230                 235                 240

Lys Ser Ala Lys His Leu Val Lys Val Leu Lys Lys Ile His Pro
                245                 250                 255

Ser Ser Arg Gly Ser Val Ser Gly Lys Pro Glu Val Asp Ser Thr Lys
                260                 265                 270

Lys Lys Phe Gln Lys Met Val Gln Val Phe His Arg Lys Val His Pro
        275                 280                 285

Glu Glu Ser Ile Met Glu Thr Lys Ile Tyr Ser Ser Val Ala Asn Pro
        290                 295                 300

Lys Ser Ser Lys Ala Asn Ser Ile Asp Leu Thr Phe Glu Lys Val Asn
305                 310                 315                 320

His Cys His Glu Ala Ser Lys Arg Cys Ile Gln Tyr Glu Leu Arg Ser
                325                 330                 335

Ser Arg Ser Ala Lys Asn Gly Glu His Trp Ile Lys Thr Asp Glu Asp
        340                 345                 350

Tyr Phe Val Leu Glu Leu
        355

<210> SEQ ID NO 17
<211> LENGTH: 386
<212> TYPE: PRT
<213> ORGANISM: Prunus persica

<400> SEQUENCE: 17

Met Gln Leu Leu Gln Trp Val His His Lys Phe Arg His Ser Ser Ile
1               5                   10                  15

Glu Pro Leu Lys Asp Leu Ser Ile Ala Gln Pro Ser Val Asp Asp Gln
            20                  25                  30

His Ser His Met Lys Ser Ser Phe Gly Ser Ser Tyr Gly Ser Thr Ser
        35                  40                  45

Leu Glu Pro Pro Lys Arg Asp Gln Glu Lys Ser Phe Ser Glu Ser Glu
    50                  55                  60

Ala Asn Arg Glu Glu Glu Thr Ser Ala Ile Ile Ser Glu Leu Phe His
65                  70                  75                  80

Gly Phe Leu Thr Ile Gly Thr Leu Gly Ser Glu Pro Ser Ile Asn Glu
                85                  90                  95

Pro Glu Thr Pro Thr Phe Ala Thr Thr Leu Glu Asn Leu Ser Glu Pro
            100                 105                 110

Lys Thr Glu Val Thr Gln Asn Asp Leu Lys Leu Ile Ser Tyr Glu Leu
        115                 120                 125

Glu Lys Phe Leu Glu Ala Glu Thr Lys Glu Gly Val Arg Ala Ser
    130                 135                 140

Ser Ala Arg Asn Ser His Ala Ser Thr Ile Thr Leu Asn Gly Lys Gln
145                 150                 155                 160

Met Glu Glu Ser Glu Asp Glu Gly Tyr Trp Thr Thr Thr Val Val Arg
                165                 170                 175

Pro Leu Lys Glu Tyr Leu Phe Gly Ser Ser Ile Glu Leu Pro Asp Thr
            180                 185                 190

Arg Ile Glu Ala Lys Lys Glu Lys Thr Ser Leu Gln Glu Leu Phe Asp
        195                 200                 205
```

```
Arg Thr Lys Met Thr Thr Glu Asn Cys Lys Glu Thr Ser Glu Ser Val
        210                 215                 220

Asp Ile Lys Ser Glu His Lys His Thr Ser Ala Met Gln Phe Met Lys
225                 230                 235                 240

Lys Ile Ile Lys Lys Leu His Ala Ser Ser Lys Ser Ser Ala Pro Cys
                245                 250                 255

Thr Gly Gly Asp Val Thr Asp Pro Val Ser Thr Arg Lys Thr Phe Gly
            260                 265                 270

Glu Ala Ser Asp Ser Val Ser Thr Lys Lys Pro His Lys Ile Leu
        275                 280                 285

Arg Met Phe His Arg Arg Ile His Pro Glu Ser Ser Thr Ala Ala Arg
    290                 295                 300

Glu Phe Val Glu Ala Glu Lys Tyr Lys Asp Lys Asn Asn Tyr Ser Ala
305                 310                 315                 320

His Gly Arg Cys Arg Glu Asn Met Met Leu Met Gly Arg Asp Asn Arg
                325                 330                 335

Arg Phe Pro Gln Gly Ala Met Ile Lys Glu Gly Thr Glu His Gly Lys
                340                 345                 350

Lys Tyr Met Asn Leu Pro Gln Tyr Arg Leu Ser Gly Ser Asn Phe Arg
                355                 360                 365

Arg Lys Gly Glu His Trp Ile Lys Thr Asp Ala Asp Tyr Leu Val Leu
            370                 375                 380

Glu Leu
385

<210> SEQ ID NO 18
<211> LENGTH: 386
<212> TYPE: PRT
<213> ORGANISM: Prunus persica

<400> SEQUENCE: 18

Met Lys Leu Leu Gly Trp Met His Arg Lys Phe Arg Gln Asn Ser Asn
1               5                   10                  15

Glu Pro Phe Lys Val Phe Val Ile Gly Gln Pro Ser Leu Asp Asp Gln
            20                  25                  30

Gln Cys Tyr Pro Lys Pro Asn Cys Gly Thr Lys Pro Phe Lys Gln Thr
        35                  40                  45

Gln Arg Asp Gln His Leu Arg Lys Ser Phe Asn Gly Leu Glu Ala Ala
    50                  55                  60

Arg Ala Glu Glu Tyr Tyr Glu Asp Glu Ser Ser Ala Ala Ala Ser
65                  70                  75                  80

Glu Leu Phe His Gly Phe Leu Ala Ile Gly Thr Leu Gly Ser Glu Gln
                85                  90                  95

Val Ile Thr Glu Pro Ser Thr Pro Thr Leu Ala Ile Ser Val Glu Asn
            100                 105                 110

Ile Thr Glu Lys Glu Thr Glu Val Thr Glu Asn Glu Leu Lys Leu Ile
        115                 120                 125

Asn Asp Glu Leu Glu Lys Val Leu Ala Ala Asp Ser Ala Lys Asp Glu
    130                 135                 140

Ile Cys Asn Asp Ser Ser Gly Arg Asn Ser His Val Ser Asn Gly Arg
145                 150                 155                 160

Ser Ser His Gly Ser Thr Ile Thr Leu Ser Gly Lys Thr Leu Glu Gly
                165                 170                 175

Ser Glu Ser Asn Gly Ile Asn Gly Thr Thr Val Cys Pro Leu Gln Gly
```

-continued

```
              180                 185                 190
Tyr Leu Phe Gly Ser Ala Tyr Glu Leu Ser Glu Thr Thr Thr Val Ala
            195                 200                 205

Lys Lys Glu His Arg Thr Ser Leu Gly Glu Leu Phe Gln Arg Thr Lys
            210                 215                 220

Leu Ala Glu Glu Ile Ser Gly Pro Lys Ser Ala Lys Glu Glu Lys Arg
225                 230                 235                 240

Ala Glu Lys Glu Ala Glu Lys Ser Ala Met His Leu Met Lys Lys Lys
                245                 250                 255

Leu Lys Lys Lys Met Leu Tyr Ala Ser Ser Arg Ser Ser Gly Gly Pro
                260                 265                 270

Ala Asp Pro Ser Ser Ala Glu Thr Lys Leu Asn Lys Ile Leu His Met
            275                 280                 285

Phe His Arg Lys Val His Pro Glu Thr Ser Ser Ala Glu Gln Lys Thr
            290                 295                 300

Gly Lys Tyr His Lys Asn Glu Asn Lys Lys Lys Thr Ser Asn Asp Gly
305                 310                 315                 320

Ala Tyr Asn Ser Gly Asp Gln Val Leu Pro Asp Glu Asp Ile Met Leu
                325                 330                 335

Tyr Pro Glu Arg Gly Phe Ser Leu Lys Gln Ser Met Arg Arg Tyr Lys
                340                 345                 350

Ser Gln Ser Asn Pro Pro Gln Phe Ala Leu Ser Ser Ile Asp Ser Asn
            355                 360                 365

Glu Asn Arg Glu His Trp Ile Lys Thr Asp Ala Asp Tyr Leu Val Leu
            370                 375                 380

Glu Leu
385
```

DRO1 RELATED GENES INFLUENCE LATERAL ROOT ORIENTATION AND GROWTH IN *ARABIDOPSIS* AND *PRUNUS* SPECIES

CROSS-REFERENCE TO PRIOR FILED APPLICATIONS

This application claims priority to U.S. Patent Application 62/403,033 filed on Sep. 30, 2016, the contents of which are incorporated herein by reference in its entirety.

SEQUENCE LISTING

The Sequence Listing submitted via EFS-Web as ASCII compliant text file format (.txt) and filed on Sep. 13, 2017, named "SequenceListing_ST25", (created on Aug. 28, 2017, 56 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

Field of the Invention

This invention relates to a gene PpeDRO1 identified from peach and the role of DEEPER ROOTING genes in controlling root orientation and overall depth of the root system of two economically important *Prunus* tree species and to new methods of manipulating root system length by overexpression of PpeDRO1.

Description of the Relevant Art

Plant productivity can be greatly influenced by root architectural traits, which makes them an important target of agricultural improvement (Lopez-Arredondo et al. 2015. F1000Research 4:651; Kong et al. 2014. *Trends Biotech.* 32:597-598). Roots are essential for uptake of water and nutrients, as well as stability within the soil. Changes to root architectural traits can alter access to different layers within the heterogeneous soil column, resulting in changes to nutrient and water availability or interaction with biotic factors. This is because resources such as water and nitrogen are found in deeper soil layers, while other nutrients such as phosphorous are more abundant in shallower strata (Lynch, J. P. 2011. *Plant Physiol.* 156:1041-1049; Lynch, J. P. 2013. *Ann. Bot.* 112:347-357). Thus, alterations in root system architecture can improve access to limiting resources.

Root system architecture refers to the spatial distribution of roots within the soil. Root system architecture changes are mediated by multiple processes, including growth rates and lengths of individual roots, the rate and extent of root branching, and the orientation, or angle, of those branches. The types of roots that contribute to root system architecture can differ between plant species. Dicots typically have taproot systems that consist of an embryonic primary root and a branching network of secondary lateral roots (LR). Monocots generally have a more complex fibrous root system. The fibrous systems also have an embryonic primary root and secondary lateral roots, but their contribution is smaller (McSteen, P. 2010. *Cold Spring Harb. Perspect. Biol.* 2:1-18; Smith and De Smet. 2012. *Philos. Trans. R. Soc. Lond. B. Biol. Sci.* 367:1441-1452). Instead, the majority of monocot root mass and volume comes from seed-borne seminal roots and/or shoot-borne crown roots (McSteen, supra; Smith and De Smet, supra; Hochholdinger and Zimmerman. 2008. *Curr. Opin. Plant Biol.* 11:70-74). Many genetic and environmental factors influence root architectural traits. Work in *Arabidopsis thaliana*, maize, and rice has uncovered a great deal of information as to root structure, the genetic components regulating root system architecture, and the close relationship between root system architecture and the soil environment (Malekkpoor Mansoorkhani et al. 2014. *Biotechnol. Genet. Eng. Rev.* 30:95-112; Wachsman et al. 2015. *New Phytol.* 208:26-38; Smith and De Smet, supra; Uga et al. 2015. *Breed Sci.* 65:111-119; Giehl et al. 2014. *J. Exp. Bot.* 65:769-778).

Past and current root system architecture research focusing on primary and lateral root growth and branching has revealed key roles for numerous genes and gene networks, multiple hormones including auxin, cytokinins, giberellins, brassinosteroids, abscisic acid (ABA), and ethylene, and soil nutrients including nitrogen and phosphorous (Satbhai et al. 2015. *J. Exp. Bot.* 66:1099-1112; De Smet, I. 2012. *New Phytol.* 193:867-873; Vermeer and Geldner. 2015. *F1000Prime Rep.* 7:32; Wachsman et al., supra). In contrast, relatively little is known about the factors that regulate root growth orientation, or angle. In *Arabidopsis*, a role for the hormone auxin was identified in influencing lateral root growth angle (Rosquete et al. 2013. *Curr. Biol.* 23: 817-822). In monocots, many quantitative trait loci have been identified for deep rooting and root angle (Uga et al., supra), however few genes have been identified as regulators of these traits. Through a quantitative trait loci analysis in rice, Uga et al. identified DEEPER ROOTING 1 (DRO1) as a regulator of root system architecture depth by modulating crown root angles (Uga et al. 2013a. *Nat. Genet.* 45:1097-1102). A rice variety containing a truncated copy of DRO1 exhibited shallow rooting, while another variety with a full-length copy had a deeper and narrower root system architecture. Transgenic introduction of an additional single or double copy of full length DRO1 resulted in incremental increases in root system depth. Importantly, the deeper rooting in rice conferred by DRO1 allowed drought avoidance, and thus increased grain yield and seed filling under drought conditions. This finding highlights the advantage for plant roots that can reach lower levels of the soil column under water-limited conditions. The ability to rapidly exploit lower soil layers is a beneficial trait in maize, as well, to optimize water capture (Lynch 2013, supra). Similarly, a recent study of tree species during a drought in Italy found deep rooting as a key trait associated with survival (Nardini et al. 2016. *Plant Cell Environ.* 39:618-627).

SUMMARY OF THE INVENTION

We have identified and isolated PpeDRO1 cDNA (SEQ ID NO:1) as the causative nucleic acid molecule for the deep rooting phenotype in *Arabidopsis* and plum and confirmed that overexpression of PpeDRO1 cDNA and increased production of PpeDRO1 result in the creation of altered root architectures such as narrow root angles in genetically altered *Arabidopsis* and deep rooting in genetically altered *Prunus* trees (and both narrow root angles and deep rooting in transgenic *Prunus*) compared to the root architecture (angles and depth) in wild-type *Arabidopsis* and *Prunus* trees.

In accordance with this discovery, it is an object of the invention to provide a method to routinely control root architecture in *Prunus* trees by overexpression of PpeDRO1 cDNA (SEQ ID NO: 1) or a DNA sequence encoding PpeDRO1 (SEQ ID NO: 2) in genetically altered *Prunus* trees or germplasm to obtain novel root architectures such as deep rooting in genetically altered *Prunus* trees while still retaining normal flower and fruit development. It is another object of the invention to provide an isolated or recombinant polypeptide (SEQ ID NO: 2) encoded by PpeDRO1 cDNA (SEQ ID NO: 1).

It is an object of this invention to have an expression vector that contains a heterologous promoter operably linked to a polynucleotide that encodes PpeDRO1 which has the amino acid sequence of SEQ ID NO: 2. It is a further object of this invention that the polynucleotide has the DNA sequence of SEQ ID NO: 1. It is another object of this invention to have a genetically altered cell containing this expression vector. It is yet another object of this invention that the genetically altered cell is a genetically altered *Prunus* plant cells and genetically altered *Prunus* plants generated from this genetically altered *Prunus* plant cell produces PpeDRO1 in increased amounts than wild-type *Prunus* plants, and that the increased amount of PpeDRO1 causes the genetically altered *Prunus* plant to have a root architecture of narrower lateral root branch angles and longer root systems compared to the lateral root branch angles and depth of root systems in the root architecture of wild-type *Prunus* plants. It is a further object of this invention that the genetically altered *Prunus* cell and the genetically altered *Prunus* plant can be *Prunus persica* (peach), *Prunus domestica* (plum), *Prunus avium* (cherry), *Prunus salicina* (Japanese plum) and/or *Prunus armeniaca* (apricot).

It is a further object of the invention to have methods of controlling root architectures in plants by generating a genetically altered plant having the expression vector described above. It is a further object that the genetically altered plant can be *P. persica*, *P. domestica*, *P. avium*, *P. salicina*, and/or *P. armeniaca*.

It is another object of the invention to have a method of producing a genetically altered *Prunus* plant having the altered characteristics of deep rooting (narrower lateral root branch angles and longer root system compared to lateral root branch angles and root system depth of a wild-type *Prunus* plant) by (i) transforming at least one wild-type *Prunus* cell with an expression vector that contains a heterologous promoter operably linked to a polynucleotide that encode PpeDRO1, such that PpeDRO1 has at least the amino acid sequence of SEQ ID NO: 2 to produce at least one transformed *Prunus* cell, (ii) selecting at least one transformed *Prunus* cell that produces an increased amount of PpeDRO1 compared to the amount of PpeDRO1 produced by a wild-type *Prunus* cell to produce a transgenic *Prunus* cell that produces an increased amount of PpeDRO1, and (iii) inducing the transgenic *Prunus* cell that produces increased amount of PpeDRO1 to grown into a genetically altered *Prunus* plant that produces increased amount of PpeDRO1 compared to the amount of PpeDRO1 produced by a wild-type *Prunus* plant, such that the increased amount of PpeDRO1 causes the genetically altered *Prunus* plant to have the altered root architecture of narrower lateral root branch angles and longer root system compared to the lateral root branch angles and root system depth of a wild-type *Prunus* plant. It is another object of this invention that the polynucleotide encoding PpeDRO1 has a DNA sequence of at least SEQ ID NO: 1. It is a further object of this invention to have a genetically altered *Prunus* plant produced by this method, as well as seed, stem, leaf, flower, pollen, fruit, cells, and progeny, so long as these genetically altered plant parts and progeny contain the heterologous promoter operably linked to the polynucleotide that encodes PpeDRO1 and can produce PpeDRO1 in increased amounts compared to the amount produced by wild-type *Prunus* plant or part or progeny.

It is an object of this invention to have a genetically altered *Prunus* cell containing an expression vector that contains a heterologous promoter operably linked to a polynucleotide that encodes PpeDRO1 which has the amino acid sequence of at least SEQ ID NO: 2. It is another object of this invention that the genetically altered *Prunus* cell can be induced to grow into a genetically altered *Prunus* plant which produces increased amount of PpeDRO1 compared to amount of PpeDRO1 produced by a wild-type *Prunus* plant, and that increased amount of PpeDRO1 causes the genetically altered *Prunus* plant to have an altered root architecture, namely narrower lateral root branch angles and longer root system, compared to the lateral root branch angles and root system depth of a wild-type *Prunus* plant. It is another object of this invention that the polynucleotide encoding PpeDRO1 has a sequence of at least SEQ ID NO: 1. Another object of this invention is a germplasm containing the genetically altered *Prunus* cell or its progeny.

Another object of the invention is a genetically altered *Prunus* plant having an altered root architecture of narrower lateral root branch angles and longer root system compared to the lateral root branch angles and root system depth of a wild-type *Prunus* plant. This genetically altered *Prunus* plant contains a heterologous promoter operably linked to a polynucleotide encoding PpeDRO1 which has the sequence of SEQ ID NO: 2, and the genetically altered *Prunus* plant produces increased amount of PpeDRO1 compared to the amount of PpeDRO1 produced by a wild-type *Prunus* plant, and the said increased amount of PpeDRO1 causes the genetically altered *Prunus* plant to have the altered root architecture of narrower lateral root branch angles and longer root system compared to the lateral root branch angles and root system depth of a wild-type *Prunus* plant. It is further object of this invention that polynucleotide (which is operably linked to the heterologous promoter) in the genetically altered *Prunus* plant has a DNA sequence of at least SEQ ID NO: 1. It is further object of this invention to have genetically altered *Prunus* plant parts such as, but not limited to, seeds, stems, leaves, flowers, pollen, fruits, cells, and germplasm, as well as progeny of the genetically altered *Prunus* plant, so long as these genetically altered plant parts and progeny contain the heterologous promoter operably linked to the polynucleotide that encodes PpeDRO1.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 2A, 2B and 2C show that AtDRO1 control lateral root orientation in *Arabidopsis*: atdro1 mutants exhibit wide branch angles and tip angles, as seen qualitatively (FIG. 2A) and quantitatively (FIG. 2B), as well as shorter primary roots (FIG. 2C). Asterisks indicate Student t-test values of p<0.05, unless otherwise noted.

FIG. 3A shows graphs of the changes in tip angles over time for wild-type and atdrol mutant. FIG. 3B shows representative images for wild-type and atdrol mutant at the indicated time points.

FIG. 4A depicts qPCR data comparing AtDRO1 expression in dissected roots and shoots and shows that AtDRO1 expression is largely root specific. FIGS. 4B, 4C, 4D, 4E, 4F, and 4G depict pAtDRO1::GUS staining in primary root and lateral root (LR) and shoot organs across 2 week old seedlings. FIG. 4H, the cartoon on the left, indicates the regions of the root where different staining patterns were found; 2-3 examples of each region are represented.

FIG. 5A shows *Arabidopsis* pAtDRO1::GUS transgenic line 2; FIG. 5B shows *Arabidopsis* pAtDRO1::GUS transgenic line 7. Asterisks indicate stage of staining pattern, referring to FIGS. 4B-4G. Black, oldest lateral roots; green, middle lateral roots; red, young lateral roots; blue, newly emerged lateral roots.

FIG. 6D shows that primary root length was shorter in Line 8, but not Line 3. Asterisks indicate Student t-test values of p<0.05, unless otherwise noted.

FIG. 7A shows qPCR data demonstrating that AtDRO1 OE Line 1 has higher relative express DRO1 expression compared to wild-type *Arabidopsis*. FIG. 7B shows qPCR data measuring native 3' UTR expression and indicating native gene silencing. FIG. 7C and FIG. 7D show that Line 1 exhibits wide lateral root branch angles, both quantitatively (FIG. 7C) and qualitatively (FIG. 7D).

FIG. 8A shows wild-type *Arabidopsis* (WT) shoot architecture. FIG. 8B show AtDRO1 OE plants with altered shoot architecture by exhibited narrower shoot branch angles, upward cauline leaf curling, shorter and "shrink-wrapped" siliques, and upward rosette leaf curling compared to WT. FIG. 8C shows that this altered shoot and leaf phenotypes were not seen in *Arabidopsis* plants overexpressing AtDRO1 lacking the C-terminal EAR-like motif (AtDRO1ΔEAR OE). FIG. 8D shows that shoot branch angles were statistically narrower in *Arabidopsis* AtDRO1 OE plants Lines 3 and 8 compared to WT. P-values from a Student t-test are indicated on the graph.

FIG. 13A shows that for a fixed shoot height, PpeDRO1 OE plums had significantly longer roots than controls (wild-type plums). FIG. 13B shows that PpeDRO1 OE plums exhibited greater shoot dry weight, and greater root dry weight as a population, compared to controls. FIG. 13C shows that the number of roots growing through the lower mesh grid in pots was significantly higher in PpeDRO1 OE plum plants when considered as a population compared to control plum plants. FIG. 13D shows a pictorial comparison between control plum and PpeDRO1 OE plum Line 2. Asterisks indicate Student t-test values of p<0.05.

DETAILED DESCRIPTION OF THE INVENTION

Figure 1:
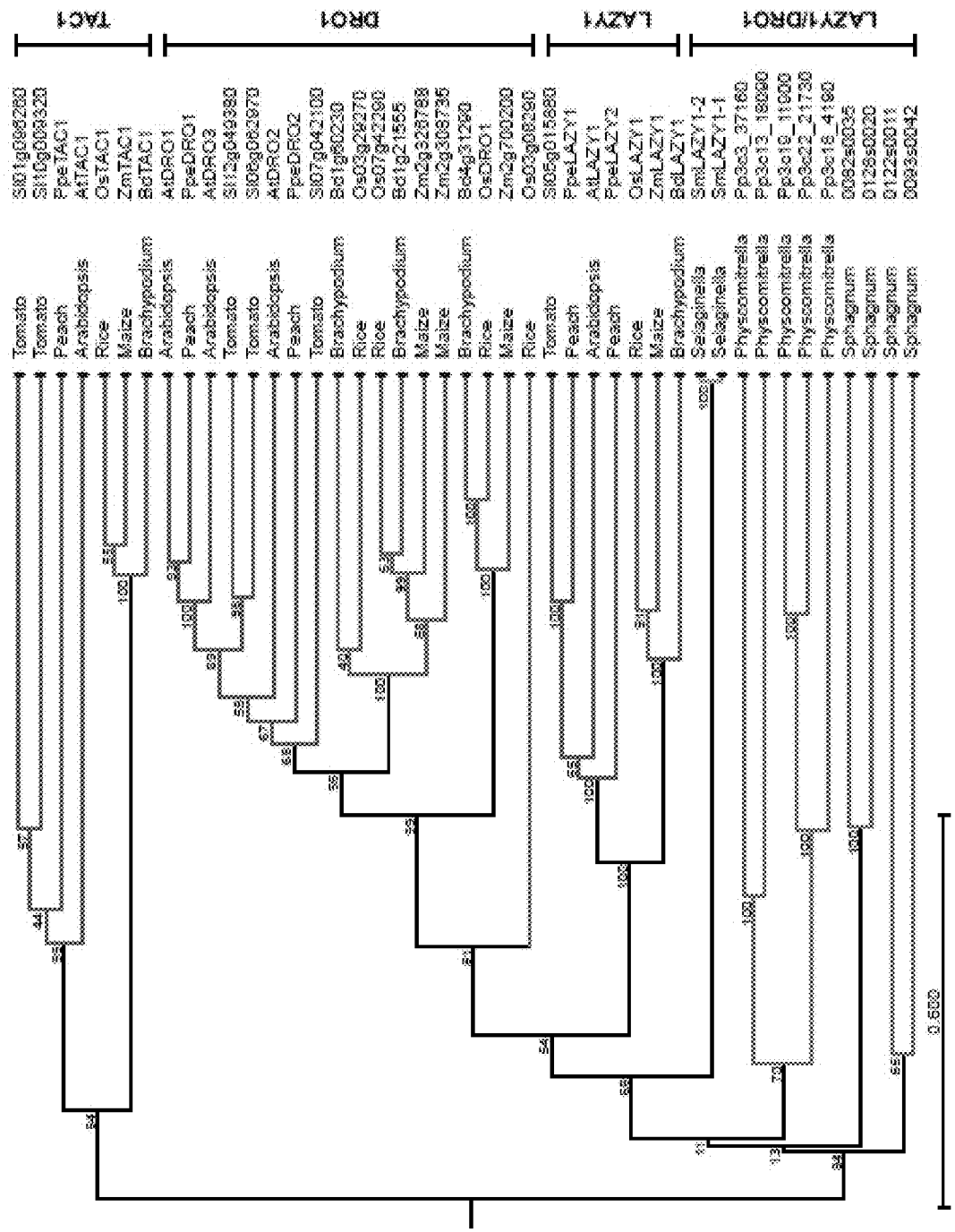
FIG. 1 depicts the phylogenetic tree of IGT genes across plant phyla. The phylogenetic tree was constructed using the UMPGA algorithm using CLC Workbench software. The alignment used to construct the tree was built using a combination of MUSCLE and manual refinement. TAC, DRO, and LAZY clades are indicated on the right. Species common names and sequence IDs are listed. Blue, dicots; magenta, monocots; orange, lycophytes; green, bryophytes.

Currently, most fruit and nut trees are grown as scions grafted to rootstocks. Rootstock varieties are generally chosen for resistance to soil pathogens and their ability to dwarf the scion. Root architectures are only selected as a general trait, as there is substantial variation. Root orientation, or angle, is an important component of the overall architecture and depth of the root system, however little is known about the genetic control of this trait. Numerous studies have been conducted in plants to understand the genetics underlying root structure. Recent reports in rice identified a role for DEEPER ROOTING 1(DRO1) in controlling the orientation of the root system, leading to positive changes in grain yields under drought conditions.

We previously proposed that DRO1 was a member of the IGT gene family (named for a conserved amino acid motif), which plays a major role in controlling lateral organ orientation (Hollender and Dardick. 2015. *New Phytol.* 206:541-556). Other IGT family members include TILLER ANGLE CONTROL 1 (TAC1) and LAZY1 which have been shown in both monocot, including rice and maize, and dicot species, including *Arabidopsis* and *Prunus persica* (peach), to control the orientation of various lateral shoot organs, including tillers, pedicels, petioles, and branches (Roychoudhry and Kepinski. 2015. *Curr. Opin. Plant Biol.* 23:124-131). Loss of TAC1 results in narrower angles in branch, tiller, leaf and flower angles compared to wild-type controls in both monocots and dicots (Yu et al. 2007. *Plant J.* 52:891-898; Ku et al. 2011. *PLoS One* 6:1-7; Dardick et al. 2013. *Plant J.* 75:618-630). In contrast, loss of LAZY1 leads to wider branch angles of these lateral organs compared to controls (Yoshihara et al. 2013. *Plant J.* 74:267-279; Li et al. 2007. *Cell Res.* 17:402-410; Dong et al. 2013. *Plant Physiol.* 163:1306-1322; Yoshihara and Lino. 2007. *Plant Cell Physiol.* 48:678-688). While the functions of these IGT genes appear to function in the same processes, the genes show a very low level of sequence similarity having only 4 or 5 conserved short protein motifs. Due to the lack of sequence conservation, the authors of the DRO1 manuscript (Uga et al., supra) did not identify the gene as an IGT family member or that counterparts exist in dicot species. This lack of sequence identity across the IGT family makes their identification in plant genomes sometimes difficult. Conservation of TAC1 and LAZY1 function across angiosperms led us to hypothesize that DRO1 has a similar function in monocots and dicots, despite having different root types and little sequence similarity.

Here we used phylogenetic analysis to evaluate DRO1-like genes across the plant kingdom and found that they form a distinct clade of the IGT gene family. Using genetic and molecular tools, we evaluated the presence, expression, and functionality of DRO1-like genes in dicots, demonstrating that DRO1-related genes in *Arabidopsis*, peach, and *Prunus domestica* (plum) influence root system architecture via changes in primary root length and lateral root angle and define the spatial expression in *Arabidopsis*. However, our data suggests that the role of DRO1 in gravity sensing in the primary root tip may not be conserved from rice to *Arabidopsis*. DRO1, present in both *Arabidopsis* and peach, displayed root-specific expression patterns. Promoter-reporter constructs revealed that AtDRO1 is predominantly expressed in both the root vasculature and root tips in a distinct developmental pattern. The lack of staining in the youngest lateral roots suggests that AtDRO1 does not affect growth orientation until roots have grown ~200-250 μm. This appears to correlate with the stage at which the lateral roots cease strict horizontal growth and can begin to explore the soil and respond to gravity (Rosquete et al., supra). The loss of staining in the oldest lateral root tips suggests that they are released from AtDRO1 control after a certain period of growth. The strong root tip staining is consistent with a role in directing growth orientation, however the normal gravitropic response in atdro1 primary roots suggests that, unlike rice, AtDRO1 may not be directly connected to gravity in *Arabidopsis* primary roots, but may function transiently to orient lateral roots to gravity. Alternatively, these genes may be involved in modulating responses to smaller changes in gravity, and a 90 degree rotation assay is above a set response threshold. Mutation of DRO1 led to more horizontal lateral root angles.

While loss of AtDRO1 led to dramatic changes in lateral root angles, overexpression had a relatively minor effect despite the high level of overexpression. This may be due to physical constraints of the root cells. For example, cells on the lower side of the emerging lateral root may not be able to compress or decrease in size enough to allow for a much more downward angle. In contrast, because lateral roots emerge and grow at a downward angle already in wild type plants, there is more space to explore above the root than below. Despite the relatively minor decrease in lateral root angle in plants with overexpressed DRO1, these small changes could lead to a large cumulative angle change over the life of the plant, particularly in perennial species.

In addition, we demonstrate that ectopic AtDRO1 expression gives architectural phenotypes in shoot organs as well as roots. Overexpression of AtDRO1 under a constitutive promoter reduced lateral root angles and resulted in shoot phenotypes including upward leaf curling, shortened siliques, and narrow lateral branch angles. A conserved C-terminal EAR-like motif found in IGT genes was required for these ectopic phenotypes. Overexpression of PpeDRO1 in plum (*Prunus domestica*) led to deeper rooting phenotypes. Collectively, these data indicate a potential application for DRO1 related genes to alter root architecture for drought avoidance and improved resource utilization.

Experiments in plums suggest that DRO1 will be a useful tool in controlling rooting capacity and depth in crops. In addition, the ability of PpeDRO1 OE plums to root on shoot-multiplication media may prove useful in developing tools for the vegetative propagation of fruit trees. Deep rooting fruit/nut trees created by DRO1 overexpression would be useful as rootstocks or as ungrafted scions for high density fruit/nut production, as well as the potential to mitigate the effects of drought. Drought avoidance strategies may be very advantageous for designing rootstocks to be grown in moisture-poor soils. Such trees would produce roots that explore deeper into the soil subsurface allowing them to tap into additional water and nutrients. Having narrower root structures would also allow the trees to be planted more closely together, as their roots would not directly compete for the same resources. Deeper roots may also provide trees with enhanced stability particularly in loose or wet soils. The implications of using DRO1 to generate designer crops and rootstocks could have a great impact on agriculture as the population increases and the climate changes.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985.

A "construct" or "chimeric gene construct" refers to a nucleic acid sequence encoding a protein, here the DRO1 protein, operably linked to a promoter and/or other regulatory sequences.

As used herein, the term "express" or "expression" is defined to mean transcription alone. The regulatory elements are operably linked to the coding sequence of the DRO1 gene such that the regulatory element is capable of controlling expression of the DRO1 genes. "Altered levels" or "altered expression" refers to the production of gene product(s) in transgenic organisms (or genetically altered organisms) in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces gene expression in root tips. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity. A "heterologous promoter" is a promoter that is operably linked to a polynucleotide to which the promoter is not normally operably linked. That is, if the polynucleotide is usually operably linked to an inducible promoter, then, when the polynucleotide is linked to a constitutive promoter, that constitutive promoter is "heterologous" to that polynucleotide. The polynucleotide could be usually operably linked to a particular inducible promoter; but when it is operably linked to a different inducible promoter, that different inducible promoter is "heterologous" to that polynucleotide.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "protein" or "polypeptide" is a chain of amino acids arranged in a specific order determined by the coding sequence in a polynucleotide encoding the polypeptide. Each protein or polypeptide has a unique function.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. "Genetically altered" is a synonym of transgenic.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful transformation of *Prunus* with PpeDRO1 is a major step in manipulating root system length by overexpression of PpeDRO1, thus ensuring the development of improved varieties of *Prunus*.

The creation of deep rooting *Prunus* trees DRO1 overexpression would be useful as rootstocks or as ungrafted scions for high density fruit production and also provides drought avoidance strategies may be very advantageous for designing rootstocks to be grown in moisture-poor soils.

Having now generally described this invention, the same will be better understood by reference to certain specific examples, which are included herein only to further illustrate the invention and are not intended to limit the scope of the invention as defined by the claims.

Example 1 Phylogeny

Phylogenetic analyses revealed that the *Arabidopsis* genome harbors three potential DRO1-like genes: AtDRO1 (At1g72490), AtDRO2 (At1g19115) and AtDRO3 (At1g17400). Based on protein sequence similarity, we placed rice DRO1 and its *Arabidopsis* homolog (At1g72490) within the IGT gene family, named for a conserved motif (FIG. 1, Uga et al. 2013b. *Nat. Genet.* 45:1097-1102; Hollender and Dardick, supra). This gene family shows relatively low levels of sequence conservation, but is marked by five short motifs as well as a conserved intron-exon structure (Dardick et al., supra). Members of the IGT family can be found throughout moss, lycophyte, monocot, and dicot species (FIG. 1, Hollender and Dardick, supra). Our phylogenetic analysis revealed the presence of multiple DRO1-related genes in both monocots and dicots. To further define the evolutionary relationships of IGT family members, we performed BLAST and conserved motif searches to identify DRO1-like genes in *Arabidopsis*, maize, rice, tomato, peach, *brachypodium, selaginella, physcomitrella* and *sphagnum*. Maximum likelihood analyses revealed that DRO1 formed a distinct IGT gene clade that was more closely related to LAZY1 than TAC1 (FIG. 1). In addition, the DRO1 clade contained two sub-clades; one consisting of monocot DRO1 genes and another that contained unknown monocot and dicot DRO1-like genes. *Arabidopsis*, peach, and tomato DRO1-like genes were more closely related to the uncharacterized family of DRO1-like genes than to rice DRO1. Consistent with previous reports, TAC1 genes were not found in primitive plant species (Dardick et al., supra). Primitive plant IGT genes formed outgroups from the LAZY and DRO clades, suggesting these clades split off from an ancient ancestor.

While the closest *Arabidopsis* protein to OsDRO1 is At1g72490 (which we named AtDRO1 here), AtDRO1 was found to be more closely related to a separate clade of uncharacterized monocot DRO1-related genes, including three rice genes (FIG. 1). The dicot DRO1-related genes group together into a single clade, however, some DRO1-related family members may have independently arisen through duplication. For example, in addition to DRO1, *Arabidopsis* contained two other DRO-related genes while peach contained only one other. These genes formed independent out-groups from AtDRO1 and PpeDRO1.

Alignments and trees were constructed using CLC genomics workbench (CLC bio). Sequences were obtained from the most recent versions of sequenced genomes available on the Phytozome web tool. Amino acid alignment was generated using MUSCLE and then manually refined. A minimum likelihood tree was constructed using the UPGMA algorithm.

Example 2 *Arabidopsis* Mutants

To determine if AtDRO1 plays a role in root growth orientation, we evaluated the phenotypic effects of putative AtDRO1 loss-of-function mutations. The Columbia (Col-0) ecotype was used as the wild-type (WT) line in all experiments. The T-DNA insertional line atdro1 mutant (SALK_201221C) and seed were obtained from *Arabidopsis* Biological Resource Center (ABRC, Ohio State University, Columbus, Ohio). For phenotyping, seed from homozygous lines were grown on large, vertically oriented plates. Seeds were surface sterilized and sown on plates containing 0.5×MS and 0.8% bactoagar. To observe root growth, seeds were sown on square plates and grown vertically. Both standard size (100×15 mm) and large (245×25 mm) growth plates were used. Once sown, seedlings were stratified at 4° C. in the dark for 2 days, then placed in growth chambers at 20° C., 16 L: 8 D, and ~100 µmol m−2 sec−1. Plates were imaged weekly for 2-4 weeks using a Canon EOS Rebel T3 camera, and lateral root branch and tip angles were manually calculated from these images using ImageJ. For gravity experiments, plates were rotated 90 degrees on the 5th day after germination, then imaged every 10 minutes. Primary root tip angles were measures with respect to the root-shoot junction. For shoot branch angles, seedlings were grown for 2 weeks on plates, then transplanted into 4-inch pots containing Metromix 360 soil, (Sun-Gro Horticulture) and grown until bolting (~6-7 inches in height). Bolts were then photographed and pressed. Angles were manually calculated by measuring the tangent of each lateral branch point.

Lateral root branch angles, tip angles, and primary root lengths were measured in 14 dpg plants. The atdro1 mutants exhibited wide lateral root growth angles with respect to gravity (FIG. 2A). Branch and tip angles were significantly increased, by an average of 18 and 25 degrees, respectively, and primary root length was 11 mm shorter on average compared to WT plants (FIGS. 2B and 2C). The wide lateral root angle phenotype led to wider root systems overall.

Figure 3A:
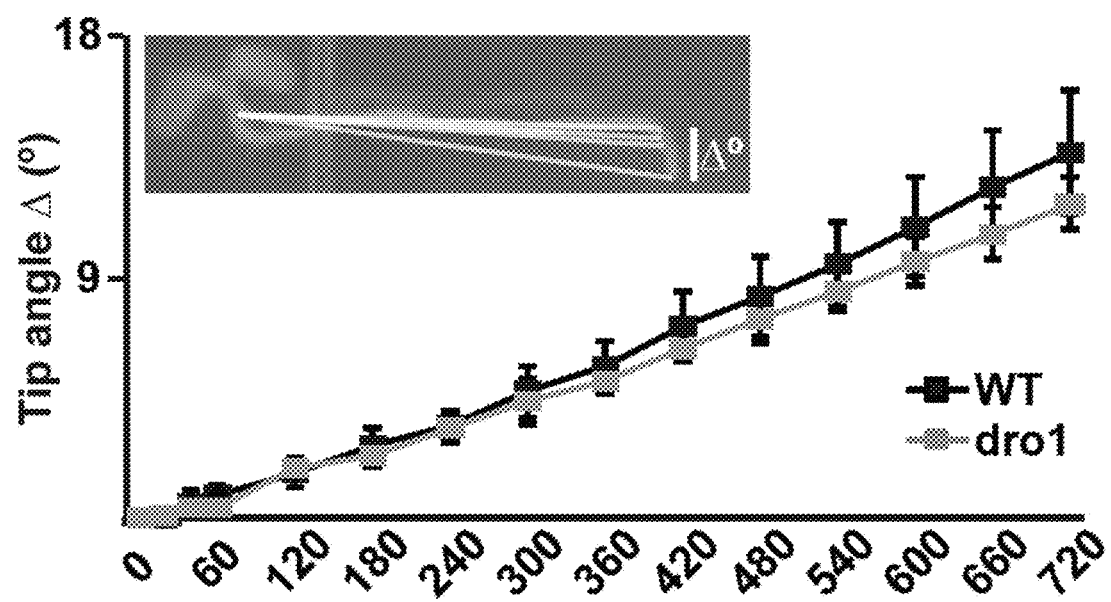
FIG. 3A and FIG. 3B depict atdrol mutant responds normally to gravity stimulus. After a 90 degree gravistimulus at 5 days post germination, images were taken of WT and atdrol seedlings. Primary root tip angle in relation to the root-shoot junction was measured at each time point for atdrol mutant (FIG. 3A, inset).
Figure 3B:
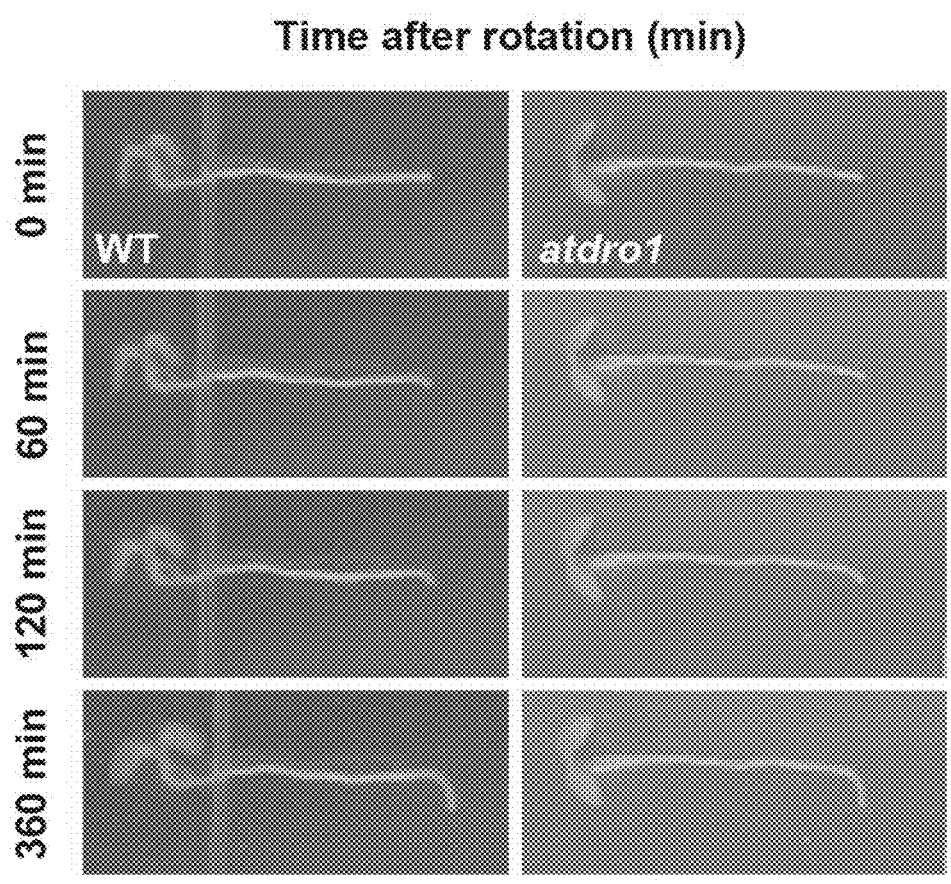

In rice, primary root tips of plants containing the truncated version of OsDRO1 were reported to display a delayed response to gravity stimulation (Uga et al. 2013b, supra). To assess whether atdro1 mutants display similar gravitropic defects, we performed gravity response assays. Mutants and wild-type control plants were grown on vertically oriented plates for 5 days, and then rotated 90 degrees. As the root grew downward toward the gravity vector, we recorded the angle of the primary root tip with respect to the root-shoot junction and gravity (FIG. 3A, inset). Neither the rate nor the degree of tip reorientation was significantly different from wild-type, however atdro1 mutants showed a non-significant difference toward the end of the experiment (FIG. 3B).

Example 3 Arabidopsis Transgenic Lines

Arabidopsis pAtDRO1::GUS transgenic lines were constructed by cloning a 2 kb fragment of the AtDRO1 promoter sequence, including the 5' UTR, upstream of the GUS (beta-glucuronidase) coding sequence in the pB1101 vectors, using SalI and SmaI restriction sites. AtDRO1 overexpression lines were made by amplifying the coding sequence of AtDRO1 (At1g72490) from Arabidopsis cDNA, and cloning downstream of the 35S promoter in our in-house pBIN-AFRS overexpression vector, using SalI and BamHI restriction sites (SEQ ID NO: 3). pBIN-AFRS was created by replacing the T-DNA region of pBIN-ARS with an artificially synthesized T-DNA that removes unwanted plasmid sequences and includes several multiple cloning sites (unpublished). Similarly, LEAR constructs were made by amplifying the AtDRO1 coding sequence, using a reverse primer that removed the final 15 bp (the EAR-like motif) from the C-terminal end of the protein. The resulting fragment was also cloned into the 35S pBIN-AFRS vector using SalI and BamHI restriction sites. Constructs were transformed into Col-0 plants using the floral dip method, and transformants were subsequently selected on 0.5×MS plates containing kanamycin.

Seedlings were grown on 0.5×MS plates and collected at 14 days past germination (dpg) for analysis. Localization of pAtDRO1gene activity in cells and tissues of the transformed seedlings was demonstrated by histological staining. The staining is very sensitive. Beta-glucuronidase (GUS) converts 5-bromo-4-chloro-3-indolyl glucuronide (X-Gluc) to a blue product. Seedlings were immersed in cold 90% acetone for 20 minutes, washed in GUS reaction buffer without X-gluc, and then immersed in GUS reaction buffer containing X-gluc. Samples were then vacuum-infiltrated for 20 minutes on ice, and subsequently placed at 37° C. in the dark for 4 hours. Seedlings were dehydrated through an ethanol series, and fixed in FAA fixative (50% Ethanol, 5% Formaldehyde, 10% Acetic acid, rest water). Light microscopy was performed using a Zeiss Axiozoom microscope.

Figure 5A:
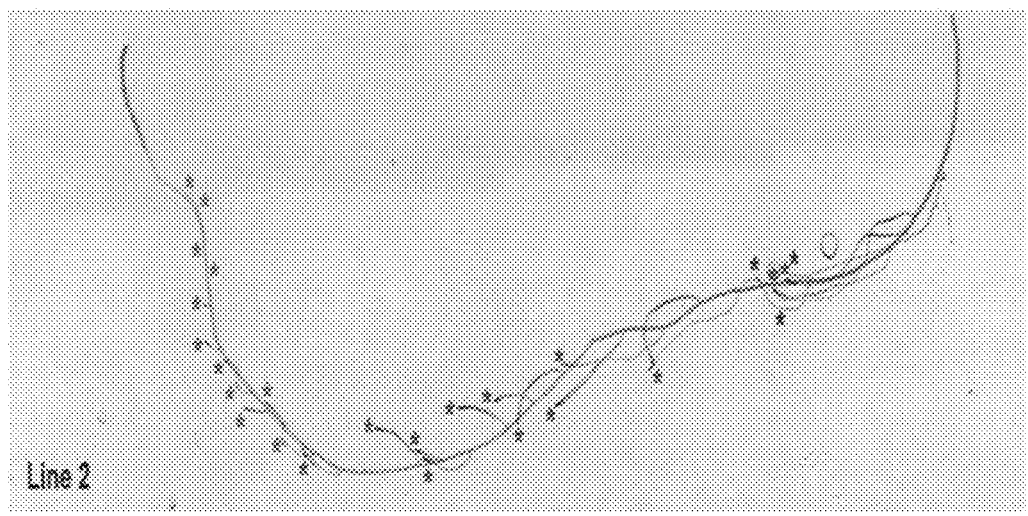
FIG. 5A and FIG. 5B depict representative full-root images of roots from two pAtDRO1::GUS seedling lines.
Figure 5B:
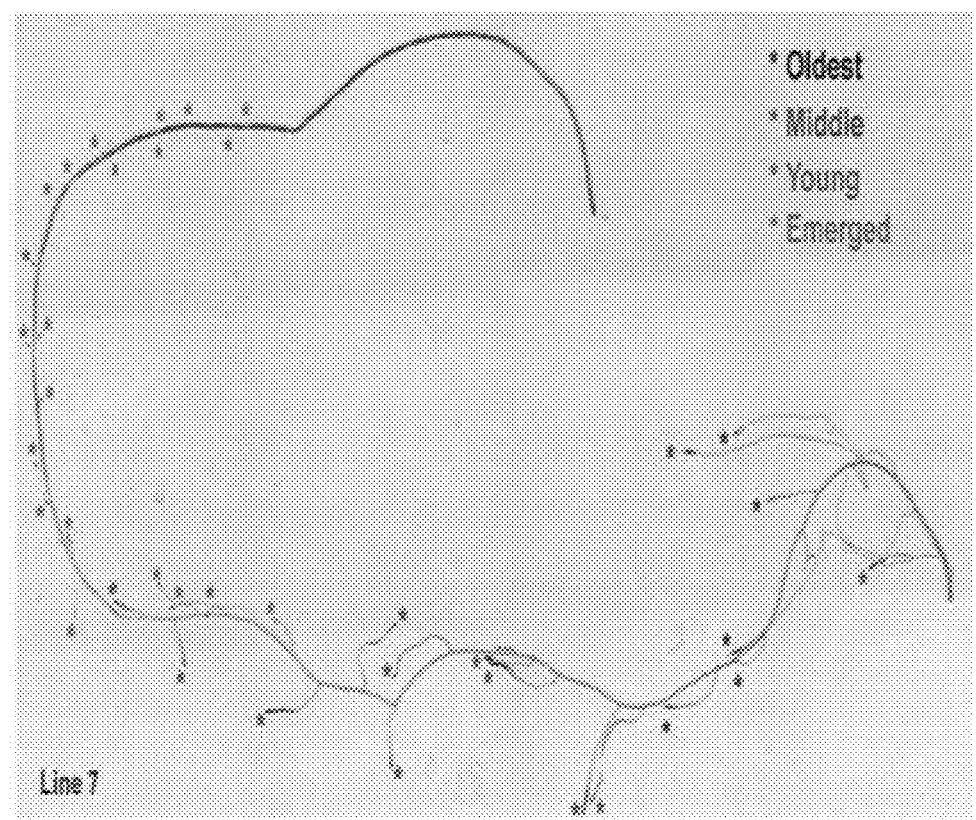

In 14 dpg seedlings, pAtDRO1::GUS staining was strongest in primary and lateral root tips, as well as root vasculature nearest the tips, with faint expression visible in the shoot vasculature of the strongest lines (FIGS. 4B-4G, FIGS. 5A and 5B). In some lines, a gradient of expression could be observed along the longitudinal axis of the youngest part of the primary root (FIGS. 5A and 5B). In the oldest part of the root system, nearest the root-shoot junction, lateral roots exhibited a gradient of staining along their longitudinal axes (FIGS. 4C and 4D). Within each plant, staining was excluded from the root tips of a subset of these oldest lateral roots (FIG. 4C). In younger lateral roots, staining was restricted to the root tips (FIG. 4E). This tip-specific expression only became apparent when lateral roots reached ~200-250 μm in length, as newly emerged lateral roots lacked staining all together (FIGS. 4F and 4G). In roots with staining along the primary root access, expression was restricted from the region surrounding a new, developing lateral root. This overall pattern was consistent with a potential role for DRO1 in root growth and root tip in situ data shown in rice (Uga et al., supra).

Figure 6A:
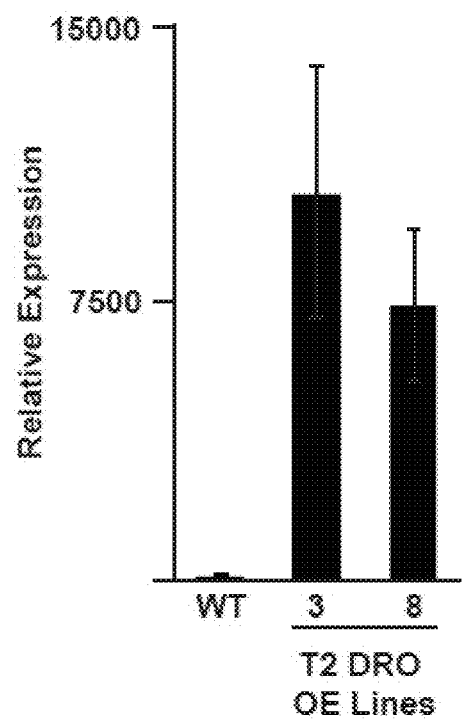
FIG. 6A presents qPCR data testing two T2 AtDRO1 overexpression (OE) lines (Lines 3 and 8) for AtDRO1 overexpression.
Figure 6B:
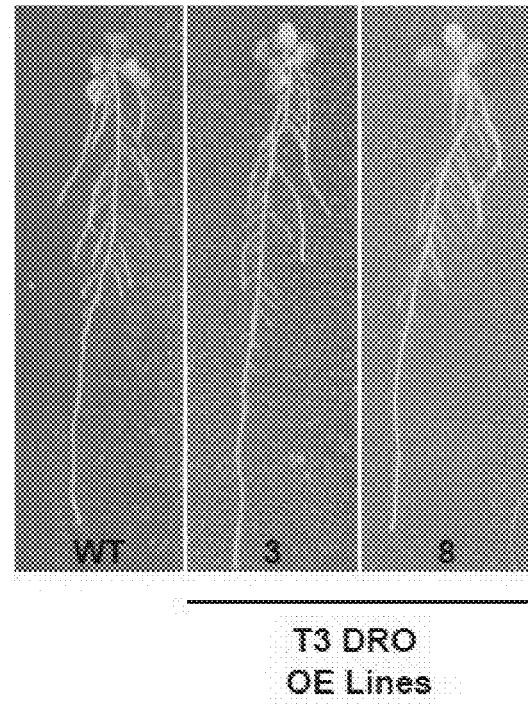
FIGS. 6B, 6C and 6D show that AtDRO1 overexpression results in narrower lateral root angles. Lines 3 and 8 were selected for subsequent experiments. Images (FIG. 6B) and graphs (FIG. 6C) show the significant decrease in lateral root branch angles of Lines 3 and 8 with respect to gravity and compared to wild-type *Arabidopsis*.
Figure 6C:
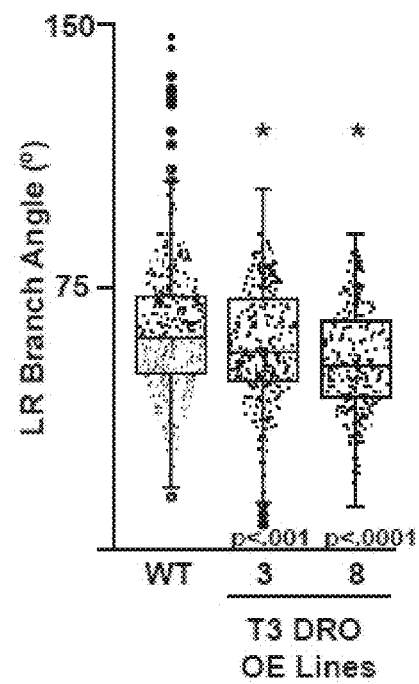
Figure 6D:
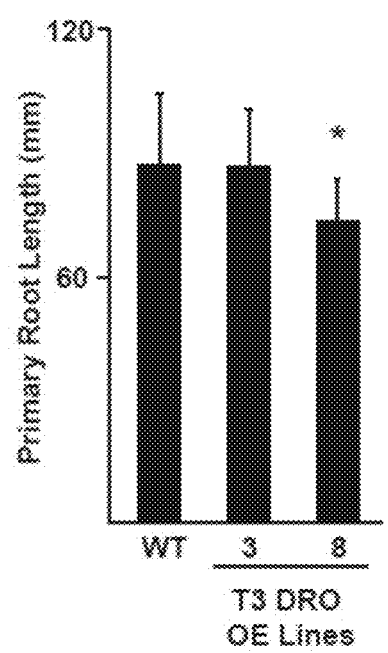

Next, we tested if overexpression of AtDRO1 is sufficient to decrease lateral root angles and increase primary root length. We generated and tested expression levels in whole seedlings of transgenic T2 overexpression (OE) lines transformed with 35S::AtDRO1 and selected representative homozygous OE lines from two lines (Line 3 and Line 4). See FIG. 6A for qPCR data. qPCR data was also obtained from other AtDRO1 OE lines (data not shown). AtDRO1 OE lines displayed a significant decrease in the average angle of lateral root branching, by 5 degrees in OE Line 3 and 9 degrees in OE Line 8 (FIGS. 6B and 6C), thus giving narrower lateral root branch angles. Primary root lengths in OE Line 3 were not significantly different from the wild-type; however, they were significantly shorter in OE Line 8 (FIG. 6D).

Figure 7A:
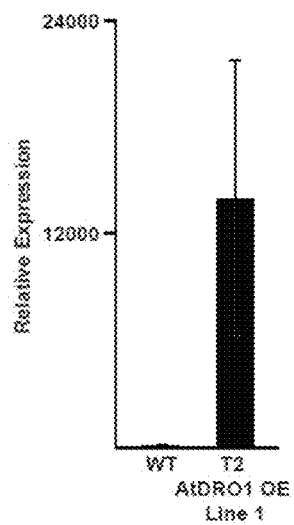
FIGS. 7A, 7B, 7C, and 7D show that AtDRO1 OE Line 1 is a silenced line exhibiting a similar phenotype to atdrol mutants.
Figure 7B:
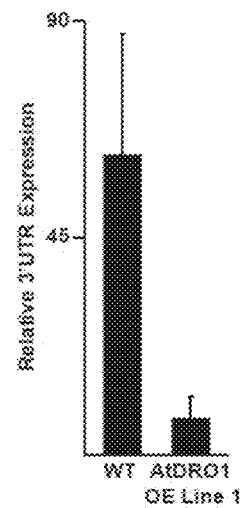
Figure 7C:
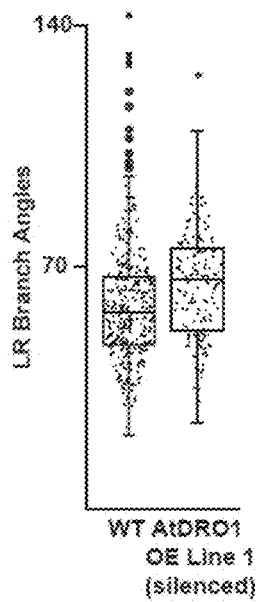
Figure 7D:
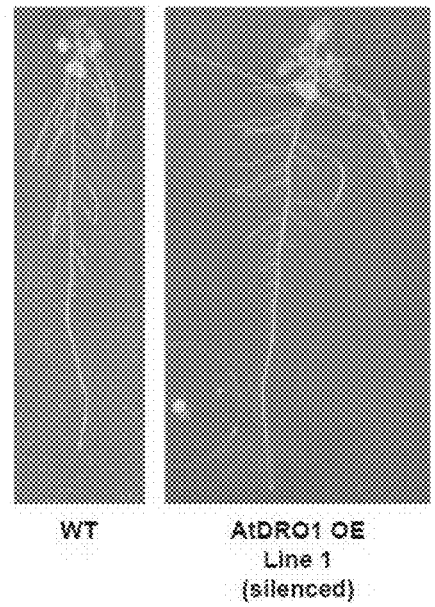

A single OE line (Line 1) exhibited horizontal roots, similar to the atdro1 T-DNA mutant line, and compared to wild-type (FIG. 7D). While the transgene was confirmed to be overexpressed via qRT-PCR compared to wild-type (FIG. 7A), we hypothesized that gene silencing was occurring. To test this, we evaluated native AtDRO1 gene expression using primers targeting the 3' UTR that was not present in the OE transgene construct. Consistent with this hypothesis, OE Line 1 showed substantially reduced native AtDRO1 expression compared with the wild-type (FIG. 7B). See also FIG. 7C for quantitative data on lower root branch angles compared to wild-type. These results are consistent with the phenotype observed in atdro1 T-DNA line.

Figure 8A:
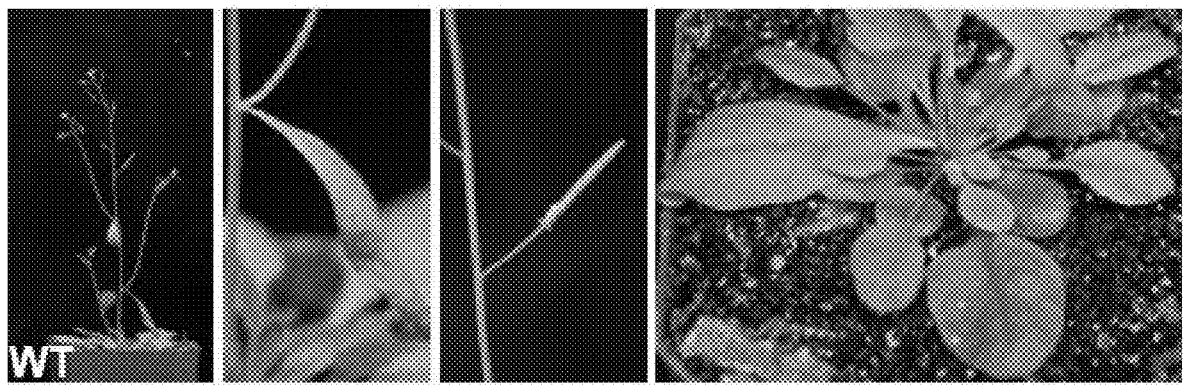
FIGS. 8A, 8B, 8C, and 8D show differences in *Arabidopsis* shoot architecture depending on AtDRO1 expression.
Figure 8B:
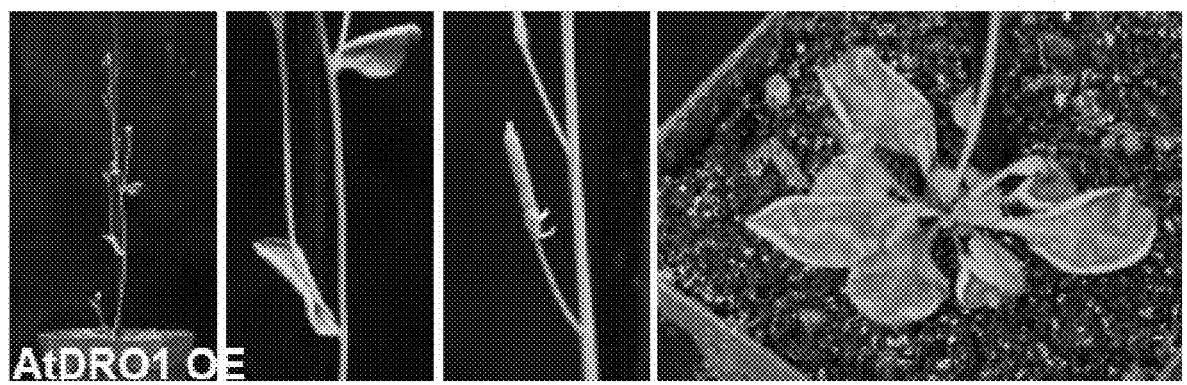
Figure 8C:
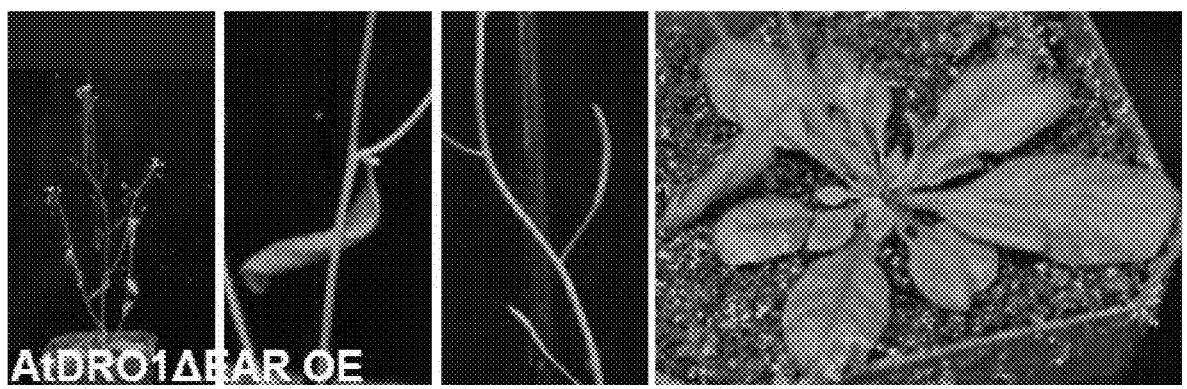
Figure 8D:
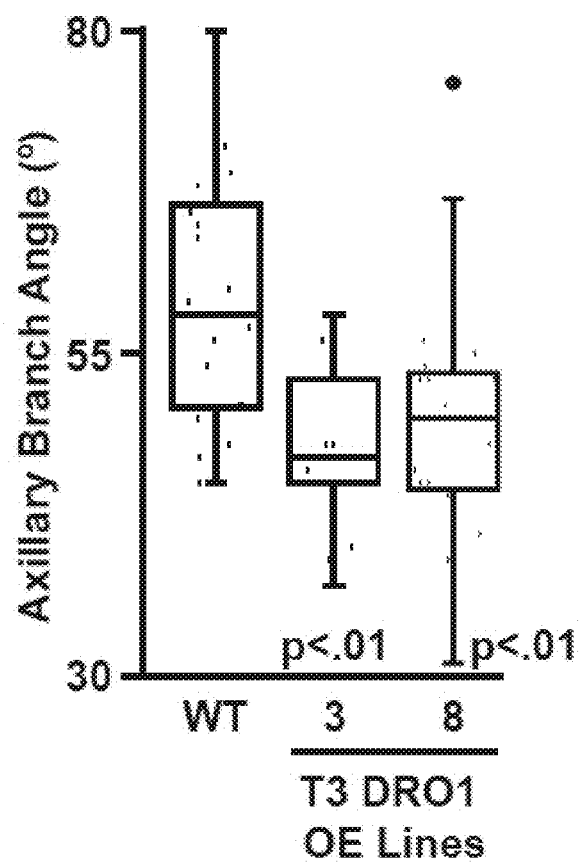

Shoots of AtDRO1 OE plants exhibited pronounced phenotypes. Both the rosette and cauline leaves displayed a distinct upward curling at the leaf margins (FIG. 8B) compared to wild-type Arabidopsis plants (WT) (FIG. 8A). With cauline leaves, this often led to the leaf curling completely around the lateral shoot above it. This may be due to differential cell expansion or division on upper and lower leaf surface. Siliques of AtDRO1 OE plants were also typically shorter than in WT, and the outlines of the seeds were more defined (FIGS. 8A and 8B). In addition, shoot branch angles were narrower by ~12 or ~10 degrees in Arabidopsis AtDRO1 OE Lines 3 and 8 (respectively) compared to WT (FIG. 8D).

Figure 9A:
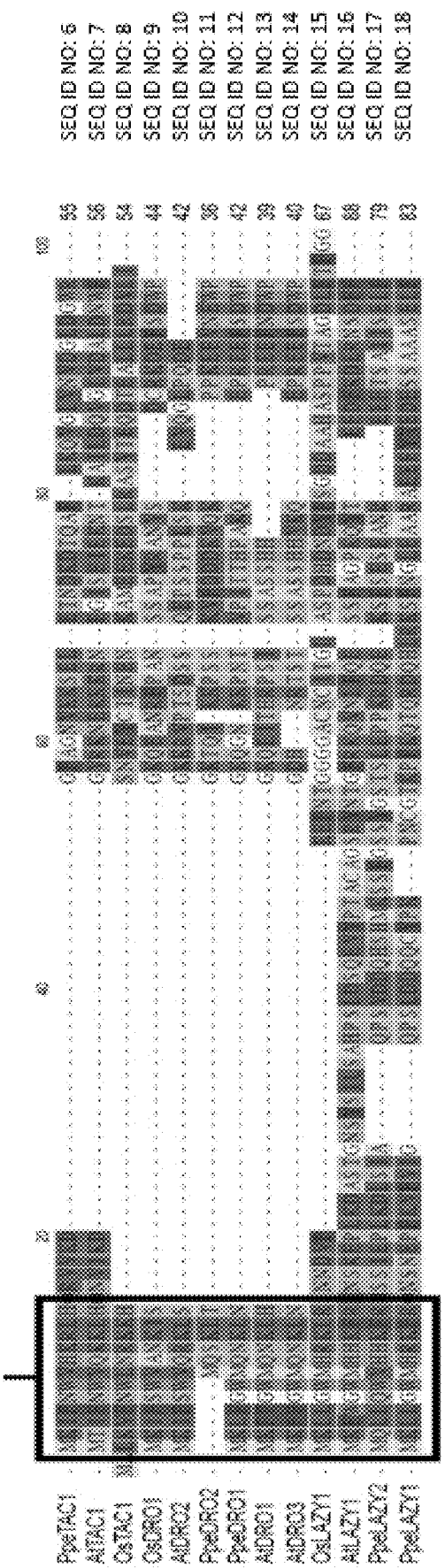
FIGS. 9A, 9B, and 9C depicts IGT family protein alignment showing conserved domains. Alignment of rice, *Arabidopsis* and peach TAC1, LAZY1 and DRO1 related genes highlights the 5 conserved domains shared among IGT family members. The fifth domain contains an EAR motif (LxLxL) in LAZY1 genes, and a similar motif in DRO1 and DRO1-related genes.
Figure 9A:
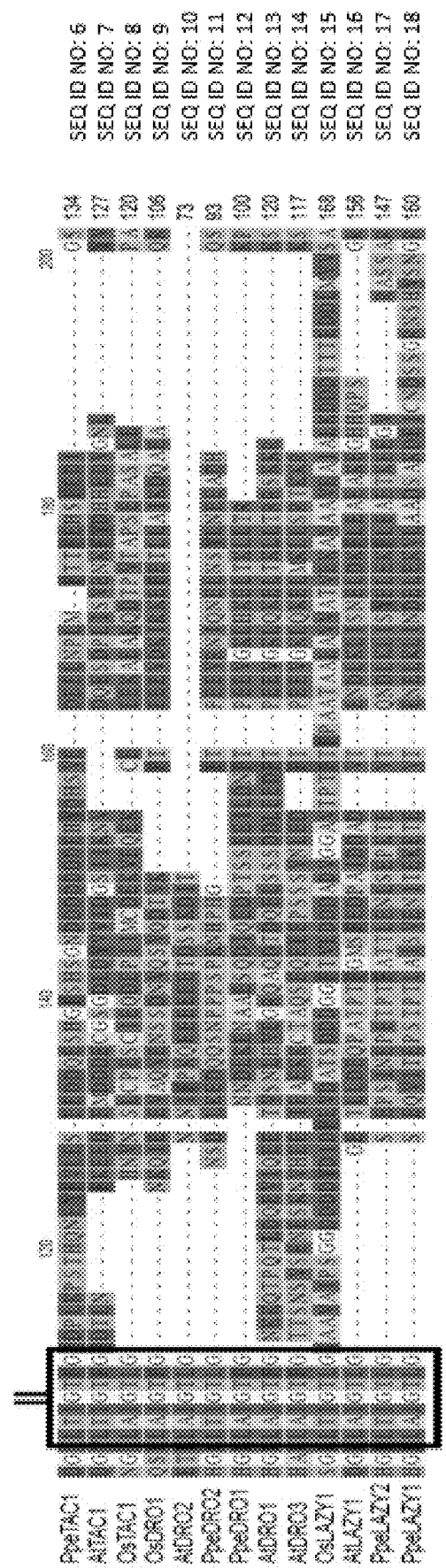
Figure 9B:
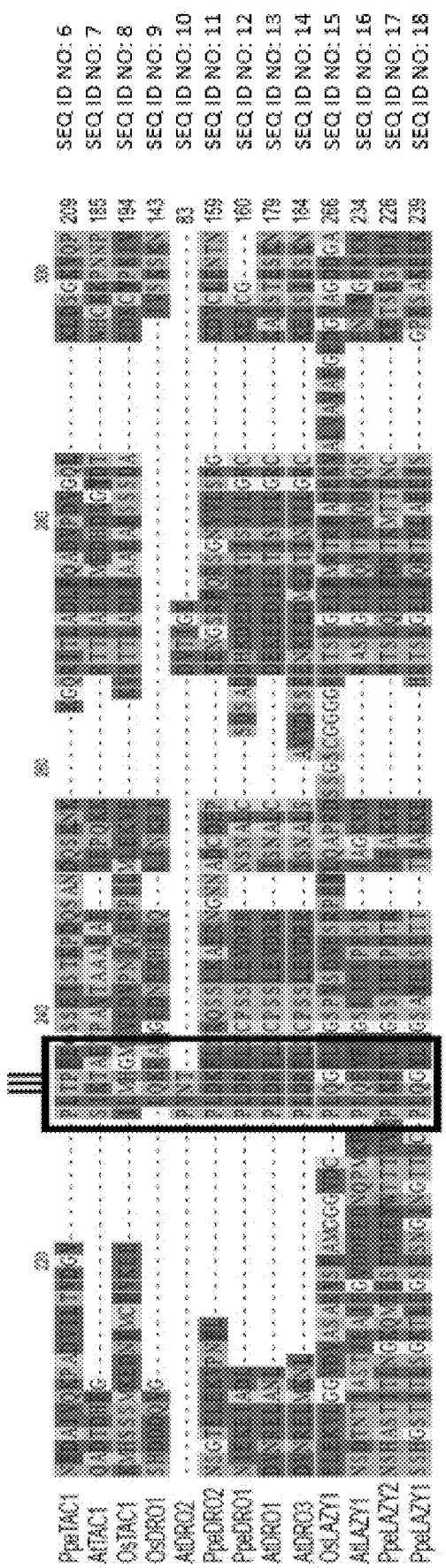
Figure 9B:
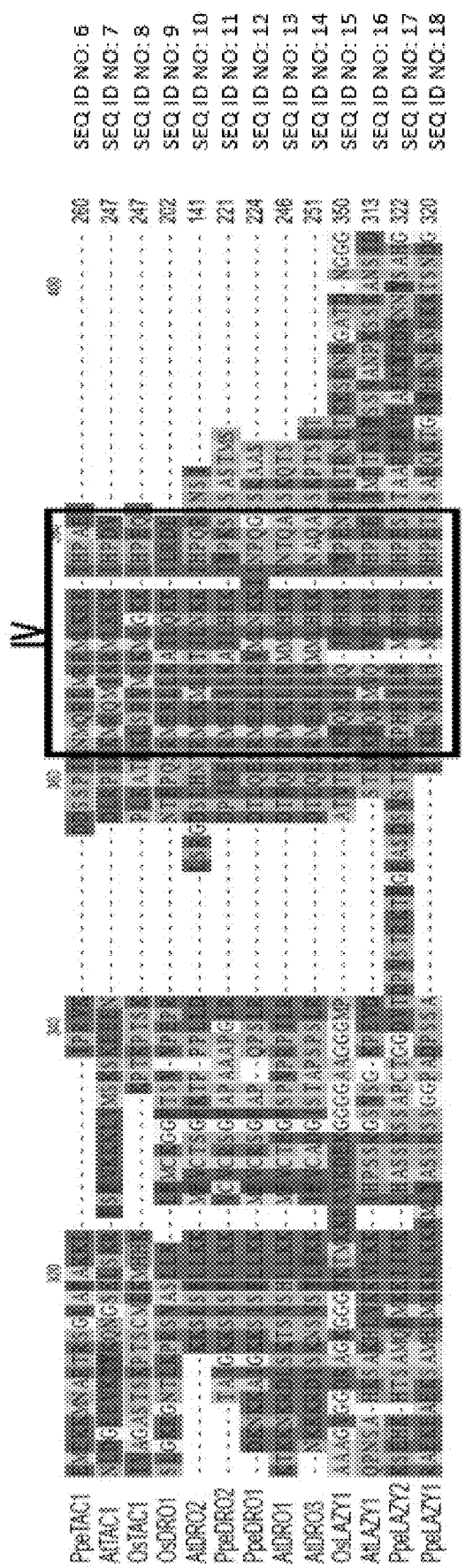
Figure 9C:
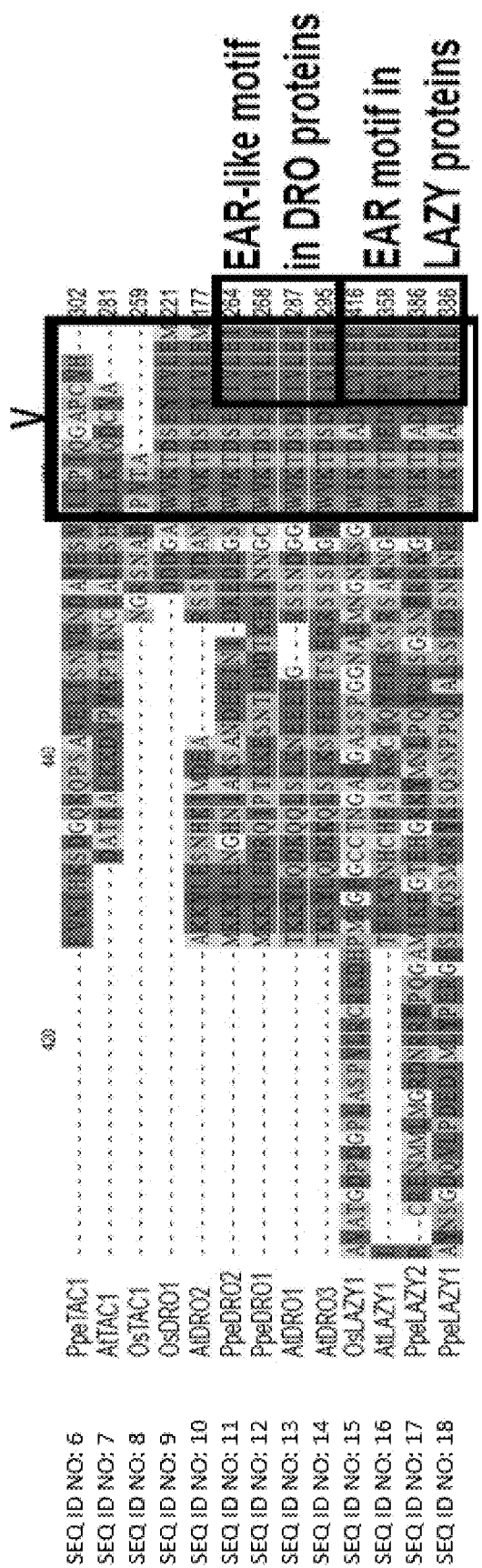
Figure 10A:
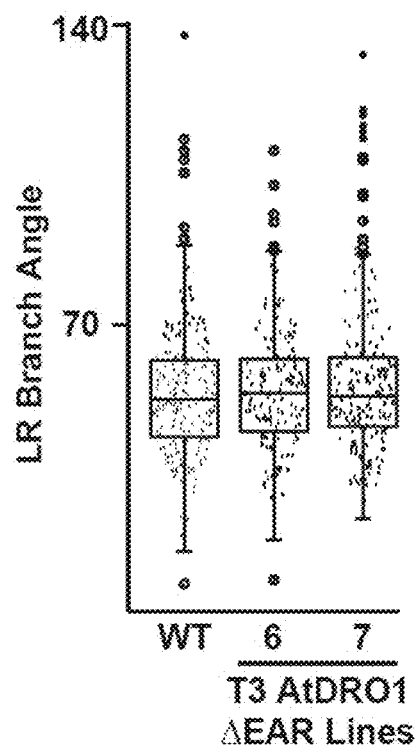
FIG. 10A and FIG. 10B show that C-terminal EAR-like motif is required for AtDRO1 OE lines to have altered root architect phenotypes. No statistical quantitative difference (FIG. 10A) or qualitative difference (FIG. 10B) was found in lateral root branch angle in *Arabidopsis* lines overexpressing AtDRO1ΔEAR, compared with WT. A Student's t-test was used to evaluate significance.
Figure 10B:
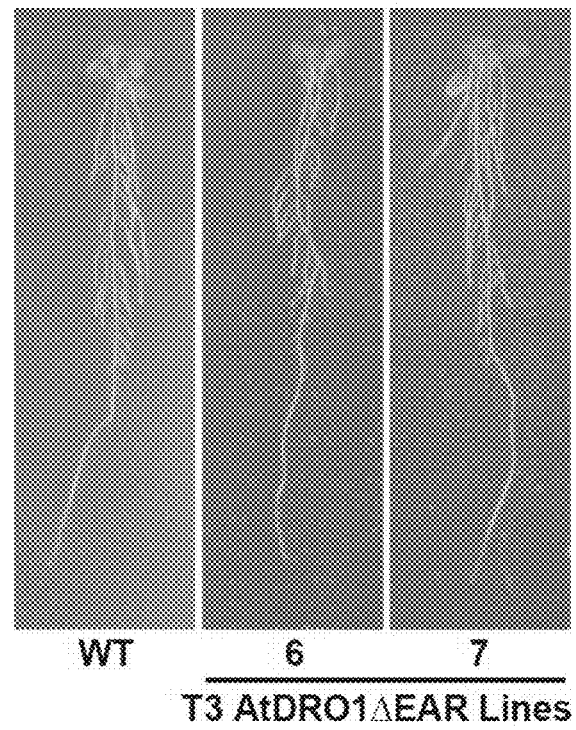

In rice, Uga et al. found that the shallow rooting IR64 varieties contain a C-terminal truncated DRO1 allele. Within the C-terminal truncated sequence are two conserved motifs—a KWVKTDS (SEQ ID NO: 4) motif of unknown function, and an IVLEI (SEQ ID NO: 5) motif that is very similar to the EAR motif present in LAZY1 (FIGS. 9A-9C). To test whether this EAR-like motif is required for AtDRO1 function, we deleted the last 5 residues (IVLEI) from AtDRO1 (AtDRO1ΔEAR) and overexpressed this truncated version in *Arabidopsis*. When grown on vertically oriented plates, we observed that, for AtDRO1ΔEAR Lines 6 and 7, the roots showed neither significant change in lateral root angle compared with wild-type *Arabidopsis* (WT) (FIGS. 10A and 10B) nor any shoot phenotype (FIG. 8C). This suggests that the EAR-like motif is required for AtDRO1 overexpression plants to have the desired altered root phenotypes.

Example 4 Plum Transformation

The functionality of PpeDRO1 was tested by generating overexpression lines in plum. Peach transformation remains highly intractable, therefore the closely related and readily transformed plum is often used for in planta assays (Petri et al. 2012. *Methods Mol. Biol.* 847:191-199). PpeDRO1 overexpression (OE) constructs were made by amplifying the coding sequence of PpeDRO1 (Ppa021925) from peach cDNA, and cloning downstream of the 35S promoter in our in-house pBIN-AFRS overexpression vector, using SalI and BamHI restriction sites. The OE construct was subsequently transformed into *Agrobacterium tumefaciens*. European plums (*Prunus domestica* L.) were transformed with the PpeDRO1 OE strain and a control (pSUC2::GUS) strain using a previously established protocol (Petri et al., supra). Briefly, cold (4° C.) stored seeds of the 'Stanley' plum variety were used for transformation. Seeds were surface sterilized with 15% commercial bleach for 15 min and washed three times with sterile water. Hypocotyls were excised from the zygotic embryos under sterile conditions using a stereomicroscope, and then sliced into 2-3 segments. After slices were immersed in an *Agrobacterium* suspension for 20 min, the transformed hypocotyl segments were cultured for 3 days in co-cultivation medium. Hypocotyl segments were then plated on antibiotic (80 mg/l kanamycin) selection medium to regenerate transgenic shoots. Recovered kanamycin resistant transgenic shoots were multiplied in multiplication medium before being transferred to rooting medium. Finally, plants were transferred to soil and acclimatized in a growth chamber for several weeks before being moved to greenhouse conditions.

Figure 11A:
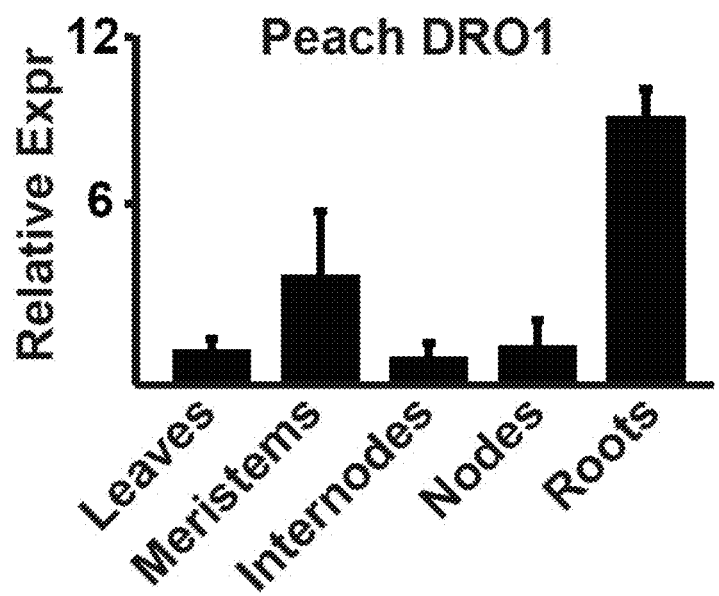
FIG. 11A shows relative expression of PpeDRO1 in the indicated plum tissue from plum plant lines overexpressing PpeDRO1 using qPCR. Highest PpeDRO1 expression occurred in roots.
Figure 11B:
FIG. 11B shows that leaf curling was seen in young transformed plum plants overexpressing PpeDRO1, similar to the upward leaf-curling phenotype in *Arabidopsis* AtDRO1 OE plants.
Figure 11C:
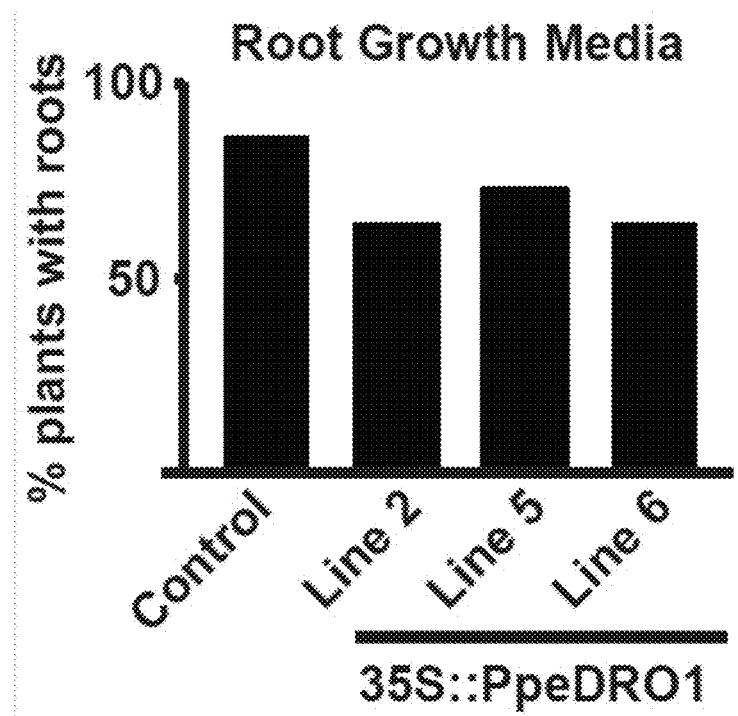
FIG. 11C and FIG. 11E show that transformed plums overexpressing PpeDRO1 in tissue culture grow roots normally on rooting medium.
Figure 11D:
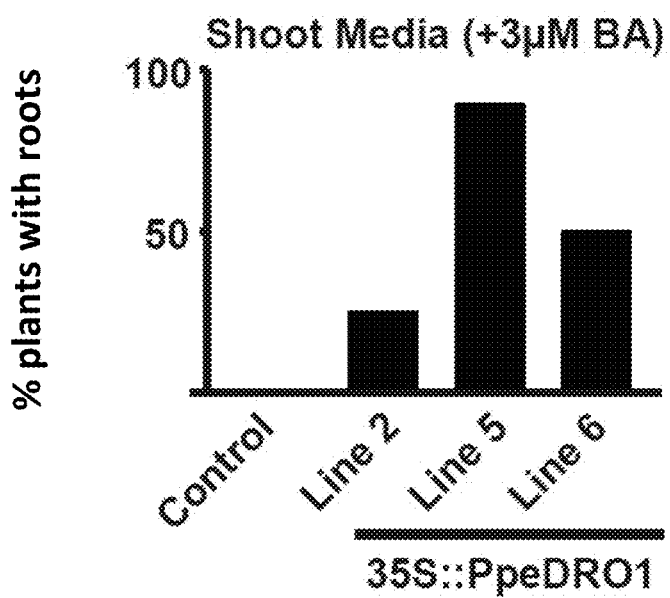
FIG. 11D and FIG. 11F show that transformed PpeDRO1 OE plums grow long roots on shoot multiplication medium containing cytokinin (BA), which is not seen in wild-type, control plum plants.
Figure 11E:
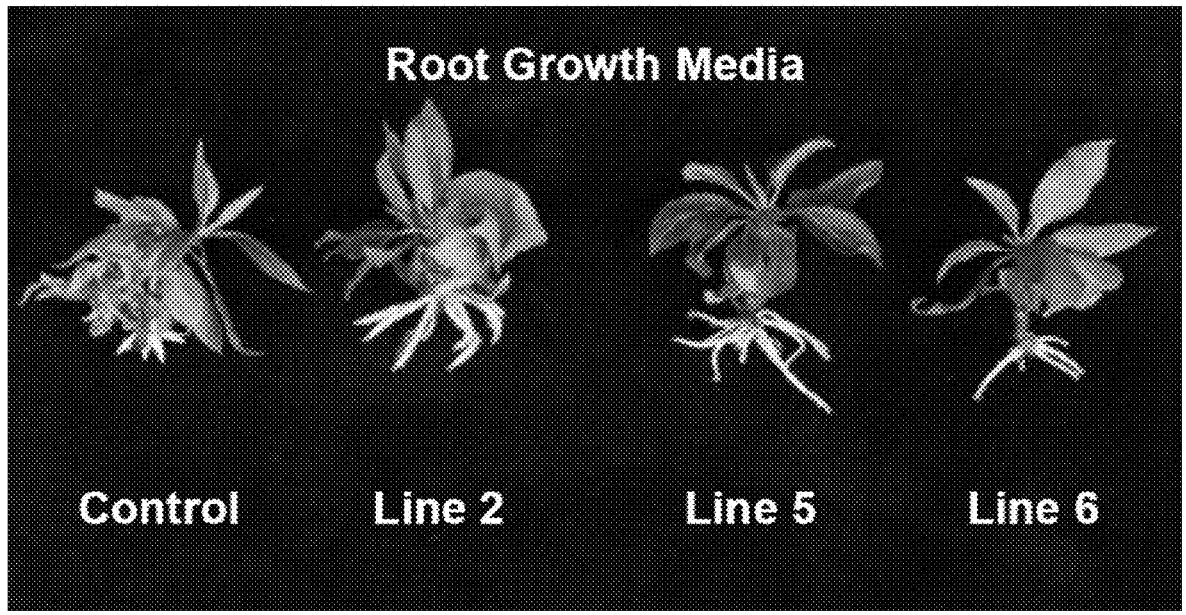
Figure 11F:
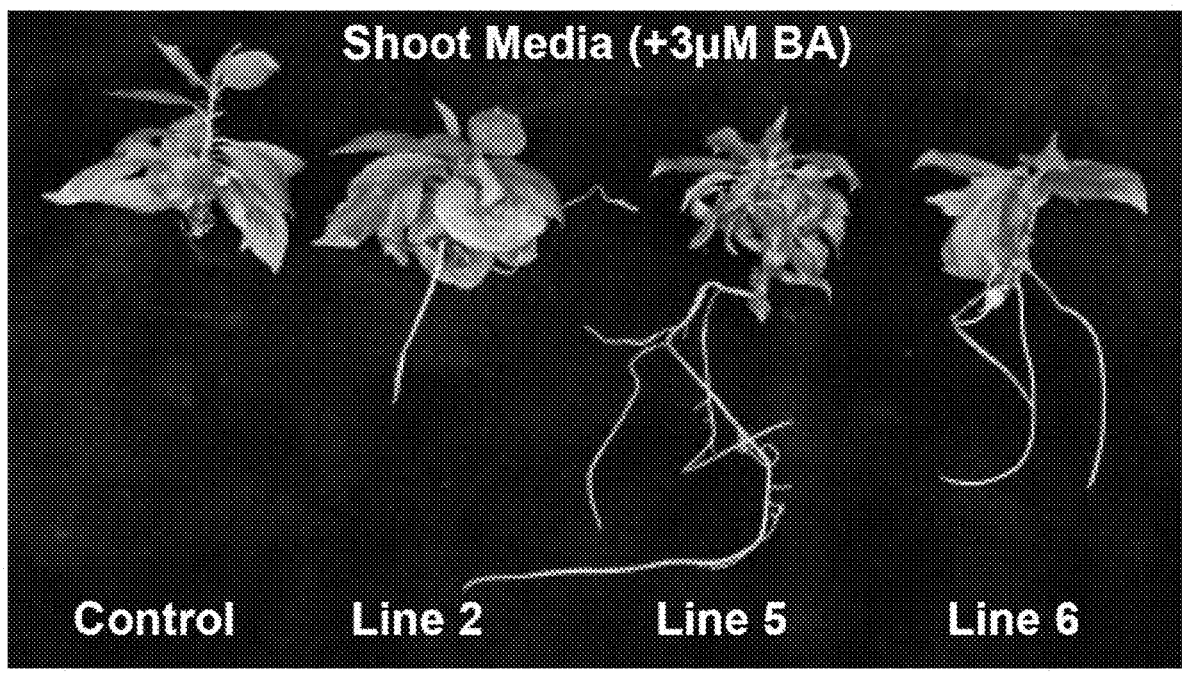

PpeDRO1 overexpression in plum results in root growth and leaf curling phenotypes. Consistent with *Arabidopsis*, expression of PpeDRO1 was highest in peach roots, about 7-14 fold higher than in leaf, node and internode samples (FIG. 11A). Shoot meristems also showed expression, about half as much as the root samples (FIG. 11A). Shoots of select lines regenerated under antibiotic selection in tissue culture displayed a similar upward leaf-curling phenotype to *Arabidopsis* AtDRO1 OE plants (compare FIG. 11B and FIG. 8B). Unlike *Arabidopsis*, the curling phenotype disappeared within 2-3 weeks after the plants were transplanted to soil. During the plum regeneration process, abnormal rooting phenotypes were also observed. The process of plum transformation involves generating plant shoots from callus, then transferring regenerated shoots first to shoot multiplication medium (FIGS. 11C and 11E), followed by transfer to rooting medium (FIGS. 11D and 11F), which stimulates root production. Shoot multiplication media contains the cytokinin BA that normally inhibits root growth. Before the transfer to rooting medium, wild-type plum regenerated shoots do not typically form roots (FIGS. 11C and 11E). Unlike control plum plants (wild-type), regenerated transgenic plum shoots overexpressing PpeDRO1 frequently formed thin roots while growing on shoot multiplication medium (FIGS. 11D and 11F).

Example 5 Plum Root Assays

Figure 12:
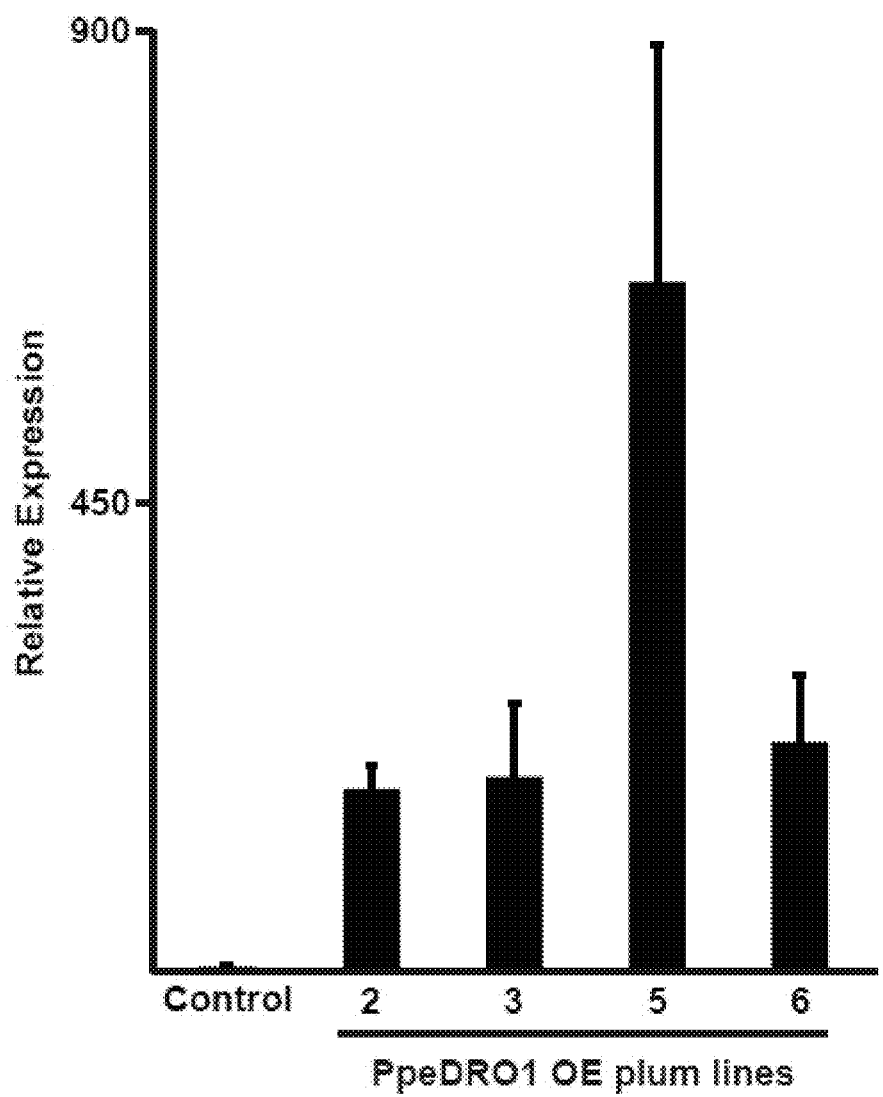
FIG. 12 depicts overexpression of PpeDRO1 in individual genetically altered plum lines. qPCR data confirm overexpression across multiple genetically altered plum lines transformed with a PpeDRO1 OE construct.

Transformed plums (genetically altered plums) that had been recovered from tissue culture and placed in soil (Metromix 360) in 3-inch pots and then placed in a growth chamber for 2-3 weeks were tested to determine whether PpeDRO1 overexpression has an effect on rooting depth. Once root systems were established in these pots, PpeDRO1 expression levels in multiple lines of recovered seedlings were confirmed. (FIG. 12) using qPCR. Then, seedlings were transplanted to 9 inch pots containing two tiers of wire mesh. Mesh grids were placed at a soil depth of 2 and 5 inches below the surface. The wire mesh grids capture the number of roots growing to each depth. Seedlings were allowed to grow in the mesh-containing pots until shoot heights reached approximately 8-12 cm. Plants were then carefully removed from soil, and the number of roots and diameter of root system growing through each mesh grid were recorded. Root and shoot lengths were recorded, and plants were subsequently dissected and dried in a drying oven overnight to measure root and shoot dry weight. For tissue culture rooting assays, shoots were generated on multiplication medium over 3-4 weeks, then transplanted to jars containing either the same shoot multiplication medium or rooting medium and allowed to grow for another 3-4 weeks.

Figure 13A:
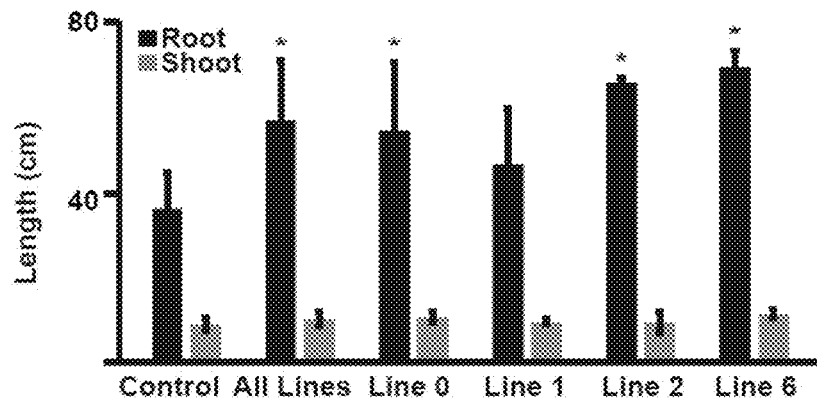
FIGS. 13A, 13B, 13C and 13D depict genetically altered plums overexpressing PpeDRO1 (PpeDRO1 OE plums) exhibit altered phenotypes from wild-type plum.
Figure 13B:
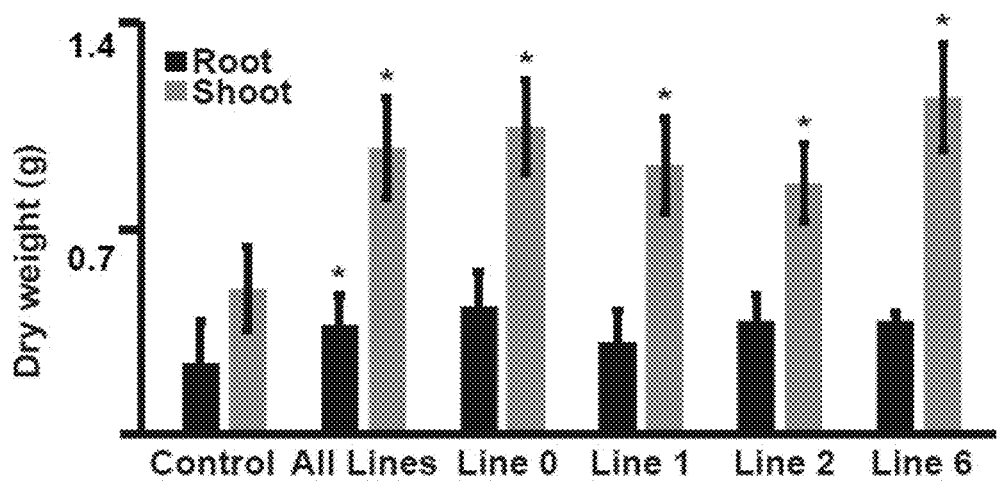
Figure 13C:
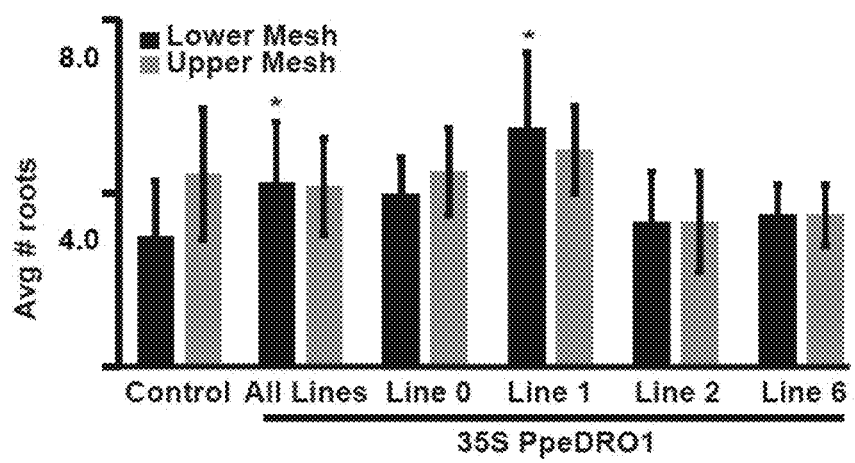
Figure 13D:
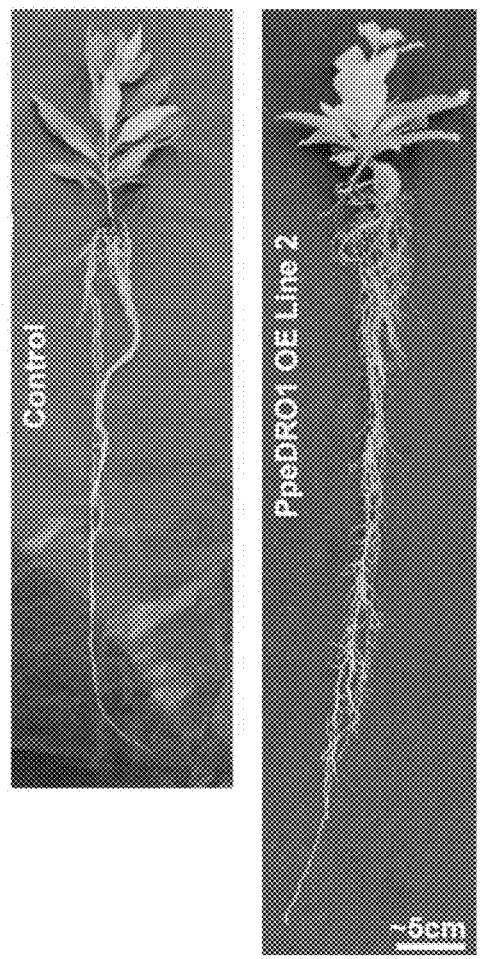

Individual seedlings reached this shoot height at different times, however this was not a genotype-specific effect. For the fixed shoot height window, the roots of genetically altered PpeDRO1 OE plums were found to be significantly longer than roots of wild-type plum (control) (FIGS. 13A and 13D). Both root dry weight (as a population) and shoot dry weight of genetically altered PpeDRO1 OE plums were greater than controls (FIG. 13B). In addition, genetically altered PpeDRO1 OE plums lines had more roots (when considered as a population) growing through the lower mesh grids than the number of roots growing through the lower mess grids of control plums (FIG. 13C). Asterisks indicate Student t-test values of p<0.05.

Example 6 AtDRO1 and PpeDRO1 Expression

Expression profiles of AtDRO1 and AtDRO1 were assessed via qualitative real-time PCR (qPCR) analysis on *Arabidopsis* seedlings. *Arabidopsis* seedlings were grown on vertical plates for 14 days, and then hand dissected to separate the shoot and the root. Each biological replicate consisted of a plate of 12 seedlings. Three biological replicates were used. *Arabidopsis* RNA was extracted using a Directzol RNA Extraction Kit (Zymogenetics).

The expression profiles of PpeDRO1 was assessed on plum tissue. Plum tissue containing the PpeDRO1 OE construct was collected from apical meristems of 2-month old plants growing in soil. Peach roots were collected for use as a standard. Peach tissue was collected and flash frozen, lyophilized for ~1 week and ground. 20-30 mg of tissue was used in the RNeasy Plant Mini Kit (Qiagen), then treated with the Ambion Turbo DNA-free kit (Ambion).

QPCR was performed as previously described by Dardick et al. (2013. *Plant J.* 75:618-630). Briefly, each reaction was run in triplicate using 50 ng of RNA in a 12 μl reaction volume, using the Superscript III Platinum SYBR Green qRT-PCR Kit (Invitrogen). The reactions were performed on a 7900 DNA sequence detector (Applied Biosystems).

Quantification for *Arabidopsis* samples was performed using a relative curve derived from a serially diluted standard RNA run in parallel. Quantification for peach and plum samples was performed using the delta Ct method, and normalized to actin.

AtDRO1 expression was evaluated in dissected roots and shoots, and AtDRO1 expression was shown to be largely root specific (FIG. 4A). qPCR data comparing PpeDRO1 expression in different peach organs indicates highest expression in roots (FIG. 11A).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An expression vector comprising a heterologous promoter operably linked to a polynucleotide encoding PpeDRO1, wherein said PpeDRO1 comprises SEQ ID NO: 2.

2. The expression vector of claim 1, wherein said polynucleotide comprises SEQ ID NO: 1.

3. A transgenic plant cell comprising the expression vector of claim 1.

4. The transgenic plant cell of claim 3, wherein said transgenic plant cell is a transgenic *Prunus* cell.

5. The transgenic *Prunus* cell of claim 4, wherein said transgenic *Prunus* cell is a transgenic cell from the group consisting of transgenic *Prunus persica*, transgenic *Prunus domestica*, transgenic *Prunus avium*, transgenic *Prunus salicina* and transgenic *Prunus armeniaca*.

6. A method of producing a genetically altered *Prunus* plant having an altered root architecture of narrower lateral root branch angles and longer root system compared to lateral root branch angles and root system depth of a wild-type *Prunus* plant, said method comprising:
   (a) transforming at least one wild-type *Prunus* cell with an expression vector comprising a heterologous promoter operably linked to a polynucleotide encoding PpeDRO1, wherein said PpeDRO1 comprises SEQ ID NO: 2 to produce at least one transformed *Prunus* cell; and
   (b) selecting at least one transformed *Prunus* cell that produces an increased amount of said PpeDRO1 compared to amount of PpeDRO1 produced by said wild-type *Prunus* cell to produce a transgenic *Prunus* cell that produces an increased amount of said PpeDRO1;
   (c) inducing said transgenic *Prunus* cell that produces said increased amount of said PpeDRO1 to grown into a genetically altered *Prunus* plant that produces said increased amount of PpeDRO1 compared to said amount of PpeDRO1 produced by said wild-type *Prunus* plant, wherein said increased amount of PpeDRO1 causes said genetically altered *Prunus* plant to have said altered root architecture of narrower lateral root branch angles and longer root system compared to said lateral root branch angles and root system depth of a wild-type *Prunus* plant.

7. The method of claim 6, wherein said polynucleotide comprises SEQ ID NO: 1.

8. A genetically altered *Prunus* plant produced by the method of claim 6 or the progeny thereof, wherein said genetically altered *Prunus* plant and said progeny produce increased amount of PpeDRO1 compared to amount of PpeDRO1 produced by a wild-type *Prunus* plant, and wherein said increased amount of PpeDRO1 causes said genetically altered *Prunus* plant and said progeny thereof to have said altered root architecture of narrower lateral root branch angles and longer root system compared to said lateral root branch angles and root system depth of a wild-type *Prunus* plant.

9. A genetically altered *Prunus* seed of the transgenic plant of claim 8, wherein said genetically altered *Prunus* seed comprises an expression vector comprising a heterologous promoter operably linked to a polynucleotide encoding PpeDRO1, wherein said PpeDRO1 comprises SEQ ID NO: 2.

10. A genetically altered *Prunus* cell comprising an expression vector comprising a heterologous promoter operably linked to a polynucleotide encoding PpeDRO1, wherein said PpeDRO1 comprises SEQ ID NO: 2, wherein a genetically altered *Prunus* plant generated from said genetically altered *Prunus* cell produces increased amount of PpeDRO1 compared to amount of PpeDRO1 produced by a wild-type *Prunus* plant, and wherein said increased amount of PpeDRO1 causes said genetically altered *Prunus* plant to have altered root architecture of narrower lateral root branch angles and longer root system compared to said lateral root branch angles and root system depth of a wild-type *Prunus* plant.

11. The genetically altered *Prunus* cell of claim 10, wherein said polynucleotide comprises SEQ ID NO: 1.

12. A genetically altered germplasm of said *Prunus* cell of claim 10.

13. A genetically altered *Prunus* plant having an altered root architecture of narrower lateral root branch angles and longer root system compared to lateral root branch angles and root system depth of a wild-type *Prunus* plant, said genetically altered *Prunus* plant comprising a heterologous promoter operably linked to a polynucleotide encoding PpeDRO1, wherein said PpeDRO1 comprises SEQ ID NO: 2, wherein said genetically altered *Prunus* plant produces increased amount of PpeDRO1 compared to amount of PpeDRO1 produced by a wild-type *Prunus* plant, and wherein said increased amount of PpeDRO1 causes said genetically altered *Prunus* plant to have said altered root architecture of narrower lateral root branch angles and longer root system compared to said lateral root branch angles and root system depth of a wild-type *Prunus* plant.

14. The genetically altered *Prunus* plant of claim 13, wherein said polynucleotide comprises SEQ ID NO: 1.

\* \* \* \* \*